US009610248B2

United States Patent
(12) United States Patent
Anderson et al.

(10) Patent No.: US 9,610,248 B2
(45) Date of Patent: Apr. 4, 2017

(54) COMPOSITIONS AND METHODS FOR TREATING INFLUENZA

(75) Inventors: David E. Anderson, Boston, MA (US); Andrei Ogrel, Russell (CA); Ronald Erwin Boch, Ottawa (CA); Jeff Baxter, Philadelphia, PA (US)

(73) Assignee: Variation Biotechnologies, Inc., Gatineau (CA)

( * ) Notice: Subject to any disclaimer, the term of this patent is extended or adjusted under 35 U.S.C. 154(b) by 0 days.

(21) Appl. No.: 13/808,155

(22) PCT Filed: Jul. 6, 2011

(86) PCT No.: PCT/US2011/043094

§ 371 (c)(1), (2), (4) Date: Jan. 3, 2013

(87) PCT Pub. No.: WO2012/006367

PCT Pub. Date: Jan. 12, 2012

(65) Prior Publication Data

US 2013/0108692 A1 May 2, 2013

Related U.S. Application Data

(60) Provisional application No. 61/361,898, filed on Jul. 6, 2010, provisional application No. 61/431,218, filed on Jan. 10, 2011.

(51) Int. Cl.

| | |
|---|---|
| ***A61K 9/127*** | (2006.01) |
| ***A61K 39/145*** | (2006.01) |
| ***A61K 47/06*** | (2006.01) |
| ***A61K 9/00*** | (2006.01) |
| ***A61K 39/12*** | (2006.01) |
| *A61K 39/00* | (2006.01) |

(52) U.S. Cl.

CPC ............ *A61K 9/127* (2013.01); *A61K 9/0019* (2013.01); *A61K 9/1271* (2013.01); *A61K 39/12* (2013.01); *A61K 39/145* (2013.01); *A61K 47/06* (2013.01); *A61K 2039/55511* (2013.01); *A61K 2039/55555* (2013.01); *A61K 2039/55561* (2013.01); *A61K 2039/55572* (2013.01); *A61K 2039/70* (2013.01); *C12N 2760/16134* (2013.01); *C12N 2760/16234* (2013.01)

(58) Field of Classification Search

None

See application file for complete search history.

(56) References Cited

U.S. PATENT DOCUMENTS

| | | | | |
|---|---|---|---|---|
| 3,952,097 | A | 4/1976 | Levy | |
| 4,024,241 | A | 5/1977 | Levy | |
| 4,349,538 | A | 9/1982 | Levy | |
| 4,352,884 | A | 10/1982 | Nakashima et al. | |
| 4,436,727 | A | 3/1984 | Ribi | |
| 4,537,769 | A * | 8/1985 | Cerini | 424/210.1 |
| 4,866,034 | A | 9/1989 | Ribi | |
| 4,877,611 | A | 10/1989 | Cantrell | |
| 4,894,228 | A | 1/1990 | Purcell et al. | |
| 4,912,094 | A | 3/1990 | Myers et al. | |
| 4,983,387 | A | 1/1991 | Goldstein et al. | |
| 5,057,540 | A | 10/1991 | Kensil et al. | |
| 5,160,669 | A | 11/1992 | Wallach et al. | |
| 5,250,236 | A | 10/1993 | Gasco | |
| 5,340,588 | A | 8/1994 | Domb | |
| 5,393,527 | A | 2/1995 | Malick et al. | |
| 5,549,910 | A | 8/1996 | Szoka, Jr. | |
| 5,567,434 | A | 10/1996 | Szoka, Jr. | |
| 5,653,996 | A | 8/1997 | Hsu | |
| 5,679,355 | A | 10/1997 | Alexander et al. | |
| 5,817,318 | A | 10/1998 | Sia et al. | |
| 5,853,753 | A | 12/1998 | Maierhofer et al. | |
| 5,858,368 | A | 1/1999 | Smith et al. | |
| 5,861,243 | A | 1/1999 | Dietrich et al. | |
| 5,876,721 | A | 3/1999 | Alexander et al. | |
| 5,879,703 | A | 3/1999 | Fountain | |
| 5,910,306 | A | 6/1999 | Alving et al. | |
| 5,919,480 | A * | 7/1999 | Kedar et al. | 424/450 |
| 5,948,410 | A | 9/1999 | Van Scharrenburg et al. | |
| 5,962,298 | A | 10/1999 | Fiers et al. | |

(Continued)

FOREIGN PATENT DOCUMENTS

| | | | |
|---|---|---|---|
| CA | 2258907 | A1 | 12/1997 |
| EP | 0413637 | A1 | 2/1991 |

(Continued)

OTHER PUBLICATIONS

International Search Report for PCT/US2011/043094 dated Feb. 3, 2012, published as WO 2012/006367 (4 pages).
Written Opinion for PCT/US2011/043094 dated Feb. 3, 2012, published as WO 2012/006367 (10 pages).
Uchegbu et al., Non-ionic surfactant based vesicles (niosomes) in drug delivery, in International Journal of Pharmaceuticals,172:33-70 (1998).
Collins, et al., Non-Ionic Surfactant Vesicle Formulation of Stibogluconate For Canine Leishmaniasis, J. Pharm. Pharmacol., 42:53P (1990).
International Preliminary Report on Patentability for PCT/US2011/043094 dated Mar. 14, 2013, published as WO 2012/006367 (8 pages).
Jurk, et al., Modulating Responsiveness of Human TLR7 and 8 to Small Molecule Ligands With T-rich Phosphorothiate Oligodeoxynucleotides, Eur J Immunol., 36(7):1815-26 (2006).
Kirby and Gregoriadis, Dehydration-Rehydration Vesicles: A Simple Method for Hight Yield Drug Entrapment in Liposomes, Biotechnology, 2:979-984 (1984).

(Continued)

*Primary Examiner* — Frederick Krass
*Assistant Examiner* — Celeste A Roney
(74) *Attorney, Agent, or Firm* — Choate, Hall and Stewart LLP; Charles E. Lyon; Rolando Medina

(57) ABSTRACT

The present disclosure provides compositions and methods useful for treating influenza. As described herein, provided compositions and methods are based on the development of certain compositions that include an influenza virus hemagglutinin antigen in combination with lipid vesicles that include a non-ionic surfactant (NISVs) and optionally an adjuvant. In certain embodiments, provided compositions remain potent even when they are not stored in a standard cold-chain system (i.e., they are thermostable).

63 Claims, 14 Drawing Sheets

(56) References Cited

U.S. PATENT DOCUMENTS

| | | | |
|---|---|---|---|
| 5,977,081 | A | 11/1999 | Marciani |
| 6,005,099 | A | 12/1999 | Davies et al. |
| 6,080,725 | A | 6/2000 | Marciani |
| 6,090,392 | A | 7/2000 | Berman |
| 6,136,606 | A | 10/2000 | Chatfield |
| 6,180,110 | B1 | 1/2001 | Funkhouser et al. |
| 6,207,178 | B1 | 3/2001 | Westesen et al. |
| 6,235,888 | B1 | 5/2001 | Pachuk et al. |
| 6,248,363 | B1 | 6/2001 | Patel et al. |
| 6,287,570 | B1 | 9/2001 | Foley |
| 6,290,967 | B1 | 9/2001 | Volkin et al. |
| 6,303,347 | B1 | 10/2001 | Johnson et al. |
| 6,344,354 | B1 | 2/2002 | Webster et al. |
| 6,372,223 | B1 | 4/2002 | Kistner et al. |
| 6,383,806 | B1 | 5/2002 | Rios |
| 6,500,623 | B1 | 12/2002 | Tung |
| 6,503,753 | B1 | 1/2003 | Rios |
| 6,534,065 | B1 | 3/2003 | Makin et al. |
| 6,538,123 | B2 | 3/2003 | Barban |
| 6,541,003 | B1 | 4/2003 | Smith |
| 6,605,457 | B1 | 8/2003 | Fiers et al. |
| 6,635,246 | B1 | 10/2003 | Barrett et al. |
| 6,649,410 | B2 | 11/2003 | Rios |
| 6,653,130 | B2 | 11/2003 | Rios |
| 6,692,955 | B1 | 2/2004 | Meredith et al. |
| 6,706,859 | B1 | 3/2004 | Sorensen |
| 6,740,325 | B1 | 5/2004 | Arnon et al. |
| 6,743,900 | B2 | 6/2004 | Burt et al. |
| 6,764,840 | B2 | 7/2004 | Johnson et al. |
| 6,787,351 | B2 | 9/2004 | Chen et al. |
| 6,831,169 | B2 | 12/2004 | Pachuk et al. |
| 6,861,244 | B2 | 3/2005 | Barrett et al. |
| 6,991,929 | B1 | 1/2006 | D'Hondt |
| 7,052,701 | B2 | 5/2006 | Barrett et al. |
| 7,063,849 | B1 | 6/2006 | Thibodeau et al. |
| 7,067,134 | B1 | 6/2006 | Kang et al. |
| 7,192,595 | B2 | 3/2007 | Arnon et al. |
| 7,244,435 | B2 | 7/2007 | Lai |
| 7,262,045 | B2 | 8/2007 | Schwartz et al. |
| 7,316,813 | B2 | 1/2008 | Eichhorn |
| 7,348,011 | B2 | 3/2008 | Guntaka et al. |
| 7,361,352 | B2 | 4/2008 | Birkett et al. |
| 7,399,840 | B2 | 7/2008 | Burt et al. |
| 7,468,259 | B2 | 12/2008 | Fiers et al. |
| 7,494,659 | B2 | 2/2009 | Katinger et al. |
| 7,510,719 | B2 | 3/2009 | Dang et al. |
| 7,514,086 | B2 | 4/2009 | Arnon et al. |
| 7,527,800 | B2 | 5/2009 | Yang et al. |
| 7,537,768 | B2 | 5/2009 | Luke et al. |
| 2002/0164648 | A1 | 11/2002 | Goins et al. |
| 2003/0092145 | A1 | 5/2003 | Jira et al. |
| 2004/0011840 | A1 | 1/2004 | Lovett |
| 2004/0022840 | A1 | 2/2004 | Nagy et al. |
| 2004/0081688 | A1 | 4/2004 | Del Curto et al. |
| 2005/0042230 | A1 | 2/2005 | Anderson et al. |
| 2005/0095283 | A1 | 5/2005 | Castor et al. |
| 2005/0169979 | A1 | 8/2005 | Michaeli et al. |
| 2005/0214331 | A1 | 9/2005 | Levy |
| 2006/0121105 | A1 | 6/2006 | Barenholz et al. |
| 2006/0257852 | A1 | 11/2006 | Rappuoli et al. |
| 2007/0142315 | A1 | 6/2007 | Forsbach et al. |
| 2007/0224257 | A1 | 9/2007 | Commander et al. |
| 2007/0264273 | A1 | 11/2007 | Barenholz et al. |
| 2008/0057080 | A1 | 3/2008 | Luke et al. |
| 2008/0131466 | A1* | 6/2008 | Reed et al. ................ 424/282.1 |
| 2008/0145375 | A1 | 6/2008 | Bembridge et al. |
| 2008/0160089 | A1 | 7/2008 | Vitiello et al. |
| 2008/0181914 | A1* | 7/2008 | Eichhorn .................. 424/209.1 |
| 2008/0213461 | A1 | 9/2008 | Gill et al. |
| 2008/0268028 | A1 | 10/2008 | Zurbriggen et al. |
| 2008/0286353 | A1 | 11/2008 | Gregoriadis |
| 2009/0028903 | A1 | 1/2009 | Hanon et al. |
| 2009/0041809 | A1 | 2/2009 | Emtage |
| 2009/0081157 | A1 | 3/2009 | Kornbluth et al. |
| 2009/0081254 | A1 | 3/2009 | Vajdy et al. |
| 2009/0117141 | A1 | 5/2009 | Torres et al. |
| 2009/0155309 | A1 | 6/2009 | Friede et al. |
| 2009/0181078 | A1 | 7/2009 | Reed et al. |
| 2009/0202620 | A1 | 8/2009 | Turnell et al. |
| 2010/0062071 | A1 | 3/2010 | Loxley et al. |
| 2010/0080844 | A1 | 4/2010 | Bacon et al. |
| 2010/0129392 | A1 | 5/2010 | Shi et al. |
| 2010/0226932 | A1 | 9/2010 | Smith et al. |
| 2011/0177163 | A1 | 7/2011 | Diaz-Mitoma et al. |
| 2012/0156240 | A1 | 6/2012 | Anderson et al. |
| 2012/0177683 | A1 | 7/2012 | Anderson et al. |
| 2012/0276125 | A1* | 11/2012 | Ast et al. .................. 424/178.1 |
| 2013/0295165 | A1 | 11/2013 | Anderson et al. |
| 2013/0323280 | A1 | 12/2013 | Anderson et al. |
| 2014/0356399 | A1 | 12/2014 | Anderson |
| 2015/0079077 | A1 | 3/2015 | Kirchmeier et al. |

FOREIGN PATENT DOCUMENTS

| | | | |
|---|---|---|---|
| EP | 0 489 153 | * | 10/1992 |
| EP | 729473 | A1 | 9/1996 |
| EP | 2014279 | A1 | 1/2009 |
| GB | 2122204 | A | 1/1984 |
| WO | WO-8806882 | A1 | 9/1988 |
| WO | WO-90/02965 | A1 | 3/1990 |
| WO | WO-92/00081 | A1 | 1/1992 |
| WO | WO-9319781 | A1 | 10/1993 |
| WO | WO-95/09651 | A1 | 4/1995 |
| WO | WO-9514026 | A1 | 5/1995 |
| WO | WO-95/17210 | A1 | 6/1995 |
| WO | WO-97/04768 | A1 | 2/1997 |
| WO | WO-98/01139 | A1 | 1/1998 |
| WO | WO-9850399 | A1 | 11/1998 |
| WO | WO-01/05374 | A1 | 1/2001 |
| WO | WO-02/051390 | A2 | 7/2002 |
| WO | WO-03011223 | A2 | 2/2003 |
| WO | WO-03099195 | A2 | 12/2003 |
| WO | WO-2005/117958 | A1 | 12/2005 |
| WO | WO-2007-110776 | * | 10/2007 |
| WO | WO-2009029695 | A1 | 3/2009 |
| WO | WO-2009-091531 | * | 7/2009 |
| WO | WO-2009-155489 | * | 12/2009 |
| WO | WO-2010/033812 | A1 | 3/2010 |
| WO | WO-2011/005769 | A1 | 1/2011 |
| WO | WO-2011/005772 | A1 | 1/2011 |
| WO | WO-2012/006367 | A2 | 1/2012 |
| WO | WO-2012/006368 | A2 | 1/2012 |
| WO | WO-2012/097346 | A1 | 7/2012 |
| WO | WO-2012/097347 | A1 | 7/2012 |

OTHER PUBLICATIONS

Lavanchy, The Importance of Vlobal Surveillance of Influenza, Vaccine, 17:S24-S25 (1999).

Pick, Liposomes With a Large Trapping Capacity Prepared by Freezing and Thawing of Sonicated Phospholipid Mixtures, Arch. Biochem. Biophys., 212:186-194 (1981).

Russell and Alexander, Effective Immunization Against Cutaneous Leishmaniasis With Defined Membrane Antigens Reconstituted Into Liposomes, J. Immunol., 140:1274-1279 (1988).

International Search Report for PCT/US2011/043095 dated Jan. 19, 2012, published as WO 2012/006368 (5 pages).

Written Opinion for PCT/US2011/043095 dated Jan. 19, 2012, published as WO 2012/006368 (8 pages).

International Preliminary Report on Patentability for PCT/US2011/043095 dated Jan. 17, 2013, published as WO 2012/006368 (8 pages).

Salager, J.L., Surfactants—Types and Uses, FIRP Booklet #E300-A, Teaching Aid in Surfactant Science & Engineering, Laboratorio FIRP, Escuela de Ingenieria Quimica, Universidad de Los Andes, Mérida 5101, Venezuela, Version #2 (Jan. 30, 1999), Translation (Dec. 15, 2002).

Alexopoulou et al., Preparation and characterization of lyophilized liposomes with incorporated quercetin, J Liposome Res. 16(1): 17-25 (2006).

Alpan et al., The role of dentritic cells, B cells, and M cells in gut-oriented immune responses, J. Immunol., 166(8): 4843-4852 (2001).

(56) References Cited

OTHER PUBLICATIONS

Andre et al., Inactivated candidate vaccines for hepatitis A, Prog. Med. Virol., 37: 72-95 (1990).
Bangham et al., Diffusion of univalent ions across the lamellae of swollen phospholipids, J. Mol. Biol. 13(1): 238-252 (1965).
Chen et al., An overview of liposome lyophilization and its future potential, Journal of Controlled Release, 142: 299-311 (2010).
Chen et al., Research advances on Solid lipid nanoparticles as new drug carrier, Chinese Journal of Ethnomedicine and Ethnopharmacy, 2:7-10 (2009).
Cregg et al., High-Level Expression and Efficient Assembly of Hepatitis B Surface Antigen in the Methylotrophic Yeast, Pichia Pastoris, Biotechnology, 5: 479-485 (1987).
Fattovich, G., Natural history of hepatitis B, J. Hepatol., 39 Suppl 1: S50-S58 (2003).
Field, et al., Inducers of interferon and host resistance. II. Multistranded synthetic polynucleotide complexes, Proc. Natl. Acad. Sci. USA, 58(3): 1004-1010 (1967).
Harford et al., Expression of hepatitis B surface antigen in yeast, Dev. Biol. Stand., 54: 125-130 (1983).
Hassan, Y. et al., Immune responses in mice induced by HSV-1 glycoproteins presented with ISCOMs or NISV delivery systems, Vaccine, 14(17-18): 1581-1589 (1996).
Hilleman MR., Critical overview and outlook: pathogenesis, prevention, and treatment of hepatitis and hepatocarcinoma caused by hepatitis B virus, Vaccine, 21(32): 4626-4649 (2003).
Huckriede, A. et al., The virosome concept for influenza vaccines, Vaccine, 23 Suppl 1:S26-38 (2005).
Kasrian and Deluca, The Effect of Tertiary Butyl Alcohol on the Resistance of the Dry Product Layer During Primary Drying, Pharm. Res., 12(4): 491-495 (1995).
Kasrian and Deluca, Thermal Analysis of the Tertiary Butyl Alcohol-Water System and Its Implications on Freeze-Drying, Pharm. Res., 12(4): 484-490 (1995).
Khmelnitsky et al., Denaturation capacity: a new quantitative criterion for selection of organic solvents as reaction media in biocatalysis, European Journal of Biochem., 198: 31-41 (1991).
Lasic, D.D., Novel Applications of Lipsomes, TIBTECH, 16:307-321 (1998).
Levy et al., Inhibition of Tumor Growth by Polyinosinic-Polycytidylic Acid, Proc. Natl. Acad. Sci. USA, 62:357-361 (1969).
Li and Deng, A novel method for the preparation of liposomes: freeze drying of monophase solutions, J. Pharm. Sci., 93(6): 1403-1414 (2004).
Mao et al., Further evaluation of the safety and protective efficacy of live attenuated hepatitis A vaccine (H2-strain) in humans, Vaccine, 15(9): 944-947 (1997).
McAleer et al., Human hepatitis B vaccine from recombinant yeast, Nature, 307(5947): 178-180 (1984).
Miller et al., Hepatitis C virus shares amino acid sequence similarity with pestiviruses and flaviviruses as well as members of two plant virus supergroups, Proc. Natl. Acad. Sci., 87: 2057-2061 (1990).
Mowat, A.M., Dendritic cells and immune responses to orally administered antigens, Vaccine, 23(15): 1797-1799 (2005).
Oku, et al., Effect of serum protein binding on real-time trafficking of liposomes with different charges analyzed by positron emission tomography, Biochimica et Biophysica Acta, 1280:149-154 (1996).
Provost et al., New findings in live, attenuated hepatitis A vaccine development, J. Med. Virol., 20(2): 165-175 (1986).
Schalk et al., Estimation of the Number of Infectious Measles Viruses in Live Virus Vaccines Using Quantitative Real-Time PCR, Journal of Virological Methods, 117:179-187 (2004).
Schubert et al., Solvent Injection as a New Approach for Manufacturing Lipid Nanoparticles—Evaluation of the Method and Process Parameters, European Journal of Pharmaceuticals and Biopharmaceutics, 55:125-131 (2003).
Szoka, Jr., F. And Papahadjopoulos, D., Comparative Properties and Methods of Preparaton of Lipid Vesicles (Liposomes)1, Ann. Rev. Viophys. Bioeng., 9:467-508 (1980).
Valenzuela et al., Chemical synthesis of a gene for human epidermal growth factor urogastrone and its expression in yeast, Proc. Natl. Acad. Sci. USA, 80(24): 7461-7465 (1983).
Vangala et al., A comparative study of cationic liposome and niosome-based adjuvant systems for protein subunit vaccines: characterisation, environmental scanning electron microscopy and immunisation studies in mice, Journal of Pharmacy and Pharmacology, 58:787-799, (2006).
Varun et al., Niosomes and Liposomes—Vesicular Approach Towards Transdermal Drug Delivery, International Journal of Pharmaceutical and Chemical Sciences, 1(3): 632-644 (2012).
Verma, S. et al., Nanoparticle vesicular systems: A versatile tool for drug delivery, Journal of Chemical and Pharmaceutical Research, 2(2):496-509 (2010).
Wagner et al., Liposome Technology for Industrial Purposes, J. Drug Delivery, vol. 2011, Article ID 591325 (9 pages) (2010).
Walde et al., Enzymes Inside Lipid Vesicles: Preparation, Reactivity and Applications, Biomol. Eng., 18:143-177 (2001).
Wang et al., Solvent Injection-Lyophilization of Tert-Butyl Alcohol/Water Cosolvent Systems for the Preparation of Drug-Loaded Solid Lipid Nanoparticles, Colloids and Surfaces B: Biointerfaces, 79:254-261 (2010).
Weiner et al., Variable and hypervariable domains are found in the regions of HCV corresponding to the flavivirus envelope and NS1 proteins and the pestivirus envelope glycoproteins, Virology 180(2): 842-848 (1991).
World Health Organization, The Immunological Basis for Immunization Series, Model 7: Measles (2009).
Yan et al., Recent Advances in Liposome-Based Nanoparticles for Antigen Delivery, Polymer Reviews, 47(3): 329-344 (2007).
Hofland, H.E.J. et al., Nonionic Surfactant Vesicles: a Study of Vesicle Formation, Characterization and Stability, Journal of Colloid and Interface Science, 161(2): 366-376, Abstract Only, 2 pages. (1993).
Kumar, G.P. et al., Nonionic surfactant vesicular systems for effective drug delivery—an overview, Acta Pharmaceutica Sinica B, 1(4): 208-219 (2011).
Mann et al., Optimisation of a Lipid Based Oral Delivery System Containing A/Panama Influenza Haemagglutinin, Vaccine, 22: 2425-2429 (2004).
Tarekegn, A. et al., Niosomes in Targeted Drug Delivery: Some Recent Advances, International Journal of Pharmaceutical Sciences and Research, 1(9): 1-8 (2010).

* cited by examiner

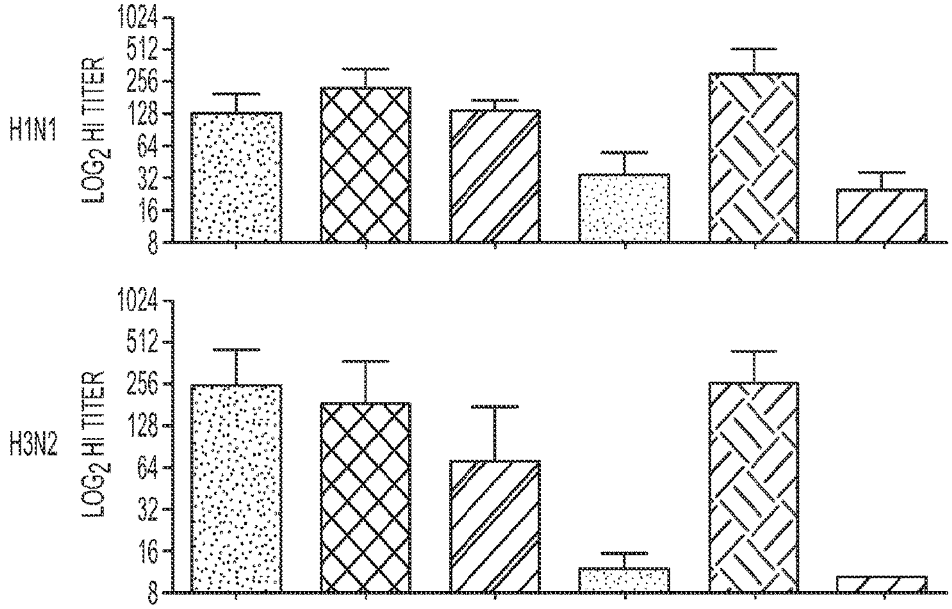

| STORAGE CONDITION | 6 MONTHS AT 4° C | | | 6 MONTHS AT 40° C | | |
|---|---|---|---|---|---|---|
| FORMULATION | REFERENCE VACCINE CONTROL (LIQUID) | NISV FORMULATED VACCINE WITH TLR-4 AGONIST ADJUVANT (LYOPHILIZED) | VACCINE WITH TLR-4 AGONIST ADJUVANT (LYOPHILIZED) | REFERENCE VACCINE CONTROL (LIQUID) | NISV FORMULATED VACCINE WITH TLR-4 AGONIST ADJUVANT (LYOPHILIZED) | VACCINE WITH TLR-4 AGONIST ADJUVANT (LYOPHILIZED) |
| TOTAL ANTIGEN (HA) CONTENT | 4.5 μg | 1.5 μg | 1.5 μg | 4.5 μg | 1.5 μg | 1.5 μg |

FIG. 6

| STORAGE CONDITION | 6 MONTHS AT 4° C | | 6 MONTHS AT 40° C | |
|---|---|---|---|---|
| FORMULATION | REFERENCE VACCINE CONTROL (LIQUID) | NISV FORMULATED VACCINE UNADJUVANTED (LYOPHILIZED) | REFERENCE VACCINE CONTROL (LIQUID) | NISV FORMULATED VACCINE UNADJUVANTED (LYOPHILIZED) |
| TOTAL ANTIGEN (HA) CONTENT | 4.5 μg | 4.5 μg | 4.5 μg | 4.5 μg |

COMPOSITIONS AND METHODS FOR TREATING INFLUENZA

CROSS REFERENCE TO RELATED APPLICATIONS

This application is the National Stage of International Application No. PCT/US2011/043094, filed Jul. 6, 2011, which claims priority to U.S. Provisional Patent Application Ser. No. 61/361,898, filed on Jul. 6, 2010 and U.S. Provisional Patent Application Ser. No. 61/431,218, filed on Jan. 10, 2011; the entirety of each of which is hereby incorporated by reference.

BACKGROUND

Influenza is a common infectious disease of the respiratory system associated with the Orthomyxoviridae family of viruses. Because of the high degree of variability of the virus, vaccination is typically required on a yearly basis with a reformulated vaccine that takes into account strain variations. The composition of the vaccine developed each year in the United States is determined by the Department of Food and Drug Administration Vaccines and the Related Biologicals Advisory Committee. The World Health Organization (WHO) similarly operates a global surveillance network of laboratories, for detection of new influenza variants, e.g., see Lavanchy, *Vaccine* 17:S24 (1999). Selection is based on antigenic analysis of recently isolated influenza viruses, the patterns of spread of antigenic variants, and the antibody responses of recently vaccinated subjects.

Influenza A and B are the two types of influenza viruses that cause epidemic human disease. Influenza A viruses are further categorized into subtypes on the basis of two surface antigens: hemagglutinin (HA) and neuraminidase (N). For example, the H1N1 subtype of influenza A viruses have a hemagglutinin type 1 antigen (H1) and a neuraminidase type 1 antigen (N1) while the H3N2 subtype have a hemagglutinin type 3 antigen (H3) and a neuraminidase type 2 antigen (N2). Influenza B viruses are not categorized into subtypes. Since 1977, influenza A (H1N1) viruses, influenza A (H3N2) viruses and influenza B viruses have been in global circulation. Vaccination is recognized as the single most effective way of preventing or attenuating influenza for those at high risk of serious illness from influenza infection and related complications. The inoculation of antigen prepared from inactivated influenza virus stimulates the production of specific antibodies. Protection is afforded only against those strains of virus from which the vaccine is prepared or closely related strains.

Each year's vaccine contains antigens from three virus strains (referred to as trivalent vaccine usually containing antigens from two type A strains and one type B strain) representing the influenza viruses that are believed likely to circulate in the coming winter. The antigenic characteristics of current and emerging influenza virus strains provide the basis for selecting strains included in each year's vaccine. The WHO reviews the world epidemiological situation annually and if necessary recommends new strains based on the current epidemiological evidence.

While influenza vaccines have been successful in reducing the incidence of influenza worldwide, there remains a need in the art for improved influenza vaccines that are stable and retain potency.

SUMMARY

The present disclosure provides compositions and methods useful for treating influenza. As described herein, provided compositions and methods are based on the development of certain compositions that include an influenza virus hemagglutinin antigen in combination with lipid vesicles that include a non-ionic surfactant (NISVs) and optionally an adjuvant. In certain embodiments, provided compositions remain potent even when they are not stored in a standard cold-chain system (i.e., they are thermostable).

In one aspect, the present disclosure provides compositions that comprise an influenza virus hemagglutinin antigen and lipid vesicles, wherein the lipid vesicles are comprised of lipids that are present in the composition in an amount that achieves a lipid:antigen weight ratio within a range of about 50:1 to about 400:1 and the lipids include a non-ionic surfactant. In certain embodiments, provided compositions are immunogenic.

In another aspect, the present disclosure provides immunogenic compositions that comprise an influenza virus hemagglutinin antigen and lipid vesicles, wherein the lipid vesicles are comprised of lipids that are present in the composition in an amount that achieves a lipid:antigen weight ratio of at least about 50:1 and the lipids include a non-ionic surfactant.

In certain embodiments, the aforementioned compositions are liquid. In certain embodiments, the aforementioned compositions are dried (e.g., lyophilized).

In another aspect, the present disclosure provides dried (e.g., lyophilized) compositions that comprise an influenza virus hemagglutinin antigen and lipid vesicles, wherein the lipid vesicles are comprised of lipids that are present in the composition in an amount that achieves a lipid:antigen weight ratio of at least about 30:1, the lipids include a non-ionic surfactant and the moisture content of the composition is less than about 2% by weight. In certain embodiments, the lipid:antigen weight ratio is at least about 40:1 or 50:1. In certain embodiments, the moisture content of provided compositions is less than about 1.9%, 1.8%, 1.7%, 1.6%, 1.5%, 1.4%, 1.3%, 1.2%, 1.1%, 1%, 0.9%, 0.8%, 0.7%, 0.6%, 0.5%, or 0.4% by weight. In certain embodiments, the moisture content of provided compositions is in the range of about 0.4% to about 2% by weight. In certain embodiments, the moisture content of provided compositions is in the range of about 0.5% to about 1.9% by weight. In certain embodiments, the moisture content of provided compositions is in the range of about 0.6% to about 1.8% by weight. In certain embodiments, the moisture content of provided compositions is in the range of about 0.7% to about 1.7% by weight. In certain embodiments, the moisture content of provided compositions is in the range of about 0.8% to about 1.6% by weight. In certain embodiments, the moisture content of provided compositions is in the range of about 0.9% to about 1.5% by weight. In certain embodiments, the moisture content of provided compositions is in the range of about 1% to about 1.4% by weight. In certain embodiments, the moisture content of provided compositions is in the range of about 0.5% to about 1% by weight. In certain embodiments, the moisture content of provided compositions is in the range of about 0.5% to about 1.5% by weight. In certain embodiments, the moisture content of provided compositions is in the range of about 0.5% to about 2% by weight. In certain embodiments, the moisture content of provided compositions is in the range of about 1% to about 1.5% by weight. In certain embodiments, the moisture content of provided compositions is in the range of about 1% to about 2% by weight. In certain embodiments, the moisture content of provided compositions is in the range of about 1.5% to about 2% by weight.

In certain embodiments, the lipid:antigen weight ratio in one of the aforementioned compositions is at least about 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1 or 300:1. In certain embodiments, the lipid:antigen weight ratio in one of the aforementioned compositions is less than about 400:1, 390:1, 380:1, 370:1, 360:1, 350:1, 340:1, 330:1, 320:1 or 310:1.

In certain embodiments, the lipid:antigen weight ratio in one of the aforementioned compositions is within a range of about 50:1 to about 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1 or 400:1. In certain embodiments, the lipid:antigen weight ratio in one of the aforementioned compositions is within a range of about 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, or 390:1 to about 400:1.

In certain embodiments, the lipid:antigen weight ratio in one of the aforementioned compositions is within a range of about 50:1 to about 100:1, about 50:1 to about 150:1, about 50:1 to about 200:1, about 50:1 to about 250:1, about 50:1 to about 300:1, about 50:1 to about 350:1, or about 50:1 to about 400:1. In certain embodiments, the lipid:antigen weight ratio in one of the aforementioned compositions is within a range of about 100:1 to about 150:1, about 100:1 to about 200:1, about 100:1 to about 250:1, about 100:1 to about 300:1, about 100:1 to about 350:1, or about 100:1 to about 400:1. In certain embodiments, the lipid:antigen weight ratio in one of the aforementioned compositions is within a range of about 150:1 to about 200:1, about 150:1 to about 250:1, about 150:1 to about 300:1, about 150:1 to about 350:1, or about 150:1 to about 400:1. In certain embodiments, the lipid:antigen weight ratio in one of the aforementioned compositions is within a range of about 200:1 to about 250:1, about 200:1 to about 300:1, about 200:1 to about 350:1, or about 200:1 to about 400:1. In certain embodiments, the lipid:antigen weight ratio in one of the aforementioned compositions is within a range of about 250:1 to about 300:1, about 250:1 to about 350:1, or about 250:1 to about 400:1. In certain embodiments, the lipid: antigen weight ratio in one of the aforementioned compositions is within a range of about 300:1 to about 350:1, or about 300:1 to about 400:1. In certain embodiments, the lipid:antigen weight ratio in one of the aforementioned compositions is within a range of about 350:1 to about 400:1. In certain embodiments, the lipid:antigen weight ratio in one of the aforementioned compositions is about 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1 or 400:1.

In certain embodiments, the aforementioned compositions exhibit less than 50% change in immunogenicity as determined by a Hemagglutination Inhibition (HAI) assay when stored for 6 months at 40° C. In certain embodiments, provided compositions exhibit less than 40%, less than 30%, less than 20%, less than 10%, less than 5% or less than 2% change in immunogenicity.

In certain embodiments, the aforementioned compositions exhibit less than 50% loss of antigen content as determined by an Enzyme-Linked Immunosorbent Assay (ELISA) when stored for 6 months at 40° C. In certain embodiments, provided compositions exhibit less than 40%, less than 30%, less than 20%, less than 10%, less than 5% or less than 2% loss of antigen content.

In certain embodiments, the aforementioned compositions are more stable when stored for 6 months at 40° C. than a reference composition that lacks the lipid vesicles. In certain embodiments, stability is based on immunogenicity as determined by an HAI assay. In certain embodiments, stability is based on antigen content as determined by an ELISA.

In yet another aspect, the present disclosure provides immunogenic compositions that comprise an influenza virus hemagglutinin antigen and lipid vesicles, wherein the lipid vesicles are comprised of lipids that include a non-ionic surfactant and the composition exhibits less than 50% change in immunogenicity as determined by an HAI assay when stored for 6 months at 40° C. In certain embodiments, provided compositions exhibit less than 40%, less than 30%, less than 20%, less than 10%, less than 5% or less than 2% change in immunogenicity.

In yet another aspect, the present disclosure provides immunogenic compositions that comprise an influenza virus hemagglutinin antigen and lipid vesicles, wherein the lipid vesicles are comprised of lipids that include a non-ionic surfactant and the composition exhibits less than 50% loss of antigen content as determined by an ELISA when stored for 6 months at 40° C. In certain embodiments, provided compositions exhibit less than 40%, less than 30%, less than 20%, less than 10%, less than 5% or less than 2% loss of antigen content.

In yet another aspect, the present disclosure provides immunogenic compositions that comprise an influenza virus hemagglutinin antigen and lipid vesicles, wherein the lipid vesicles are comprised of lipids that include a non-ionic surfactant and the composition is more stable when stored for 6 months at 40° C. than a reference composition that lacks the lipid vesicles. In certain embodiments, stability is based on immunogenicity as determined by an HAI assay. In certain embodiments, stability is based on antigen content as determined by an ELISA.

In certain embodiments, the aforementioned compositions are prepared by a method that includes: melting the lipids to produce molten lipids; combining the molten lipids with an aqueous solution that includes the influenza virus hemagglutinin antigen; and homogenizing the resulting product.

In certain embodiments, lipids (e.g., molten lipids) and aqueous solution are combined in relative amounts that achieve the desired lipid:antigen weight ratio in the resulting product (e.g., at least about 50:1 or any one of the aforementioned ranges). In certain embodiments, molten lipids are added to the aqueous solution that includes the influenza virus hemagglutinin antigen. In certain embodiments, aqueous solution that includes the influenza virus hemagglutinin antigen is added to the molten lipids.

In certain embodiments, lipids (e.g., molten lipids) and aqueous solution are combined in relative amounts and volumes that achieve a lipid concentration of at least about 10 mg/ml in the resulting product. In certain embodiments, a lipid concentration of at least about 15, 20, 25, 30, 35, 40, 45, 50, 55, 60, 65, 70, 75, 80, 85, 90 or 95 mg/ml is achieved. In certain embodiments, the lipid concentration is in a range of about 10 mg/ml to about 15, 20, 25, 30, 35, 40, 45, 50, 55, 60, 65, 70, 75, 80, 85, 90, 95 or 100 mg/ml. In certain embodiments, the lipid concentration is in a range of about 10, 15, 20, 25, 30, 35, 40, 45, 50, 55, 60, 65, 70, 75, 80, 85, 90 or 95 mg/ml to about 100 mg/ml. In certain embodiments, the lipid concentration is in a range of about 25 mg/ml to about 100 mg/ml, about 25 mg/ml to about 75 mg/ml, about 25 mg/ml to about 50 mg/ml, about 50 mg/ml to about 75 mg/ml, or about 50 mg/ml to about 100 mg/ml.

In certain embodiments, lipids (e.g., molten lipids) and aqueous solution are combined in relative amounts and volumes that achieve both the desired lipid:antigen weight ratio (e.g., at least about 50:1 or any one of the aforementioned ranges) and a lipid concentration of at least about 10 mg/ml (or any one of the other lipid concentration ranges) in the resulting product.

In certain embodiments, lipids (e.g., molten lipids) and antigen are combined in relative amounts that achieve a lipid content of at least about 5 mg per unit dose of composition (e.g., a dried unit dose of composition in a sealed container that is being stored prior to rehydration). In certain embodiments, a lipid content of at least about 6, 7, 8, 9, 10, 15, 20, 25, 30, 35, 40, 45 or 50 mg per unit dose of composition is achieved. In certain embodiments, the lipid content is in a range of about 5 mg to about 50 mg, about 5 mg to about 40 mg, about 5 mg to about 30 mg, about 10 mg to about 50 mg, about 10 mg to about 40 mg, about 10 mg to about 30 mg, about 20 mg to about 50 mg, about 20 mg to about 40 mg, or about 20 mg to about 30 mg.

In certain embodiments, lipids (e.g., molten lipids) and antigen are combined in relative amounts that achieve both the desired lipid:antigen weight ratio (e.g., at least about 50:1 or any one of the aforementioned ranges) and a lipid content of at least about 5 mg per unit dose (or any one of the other lipid content ranges).

In certain embodiments, lipids (e.g., molten lipids) and aqueous solution are combined in relative amounts and volumes that achieve the desired lipid:antigen weight ratio (e.g., at least about 50:1 or any one of the aforementioned ranges), a lipid content of at least about 5 mg per unit dose (or any one of the other lipid content ranges) and a lipid concentration of at least about 10 mg/ml (or any one of the other lipid concentration ranges) in the resulting product.

In yet another aspect, the present disclosure provides compositions that comprise an influenza virus hemagglutinin antigen and lipid vesicles, wherein the lipid vesicles are comprised of lipids that include a non-ionic surfactant and the compositions are prepared by a method that includes: melting the lipids to produce molten lipids; combining the molten lipids with an aqueous solution that includes the influenza virus hemagglutinin antigen; and homogenizing the resulting product, wherein the molten lipids and aqueous solution are combined in relative amounts that achieve the desired lipid:antigen weight ratio (e.g., at least about 50:1 or any one of the aforementioned ranges) in the resulting product. In certain embodiments, molten lipids are added to the aqueous solution that includes the influenza virus hemagglutinin antigen. In certain embodiments, aqueous solution that includes the influenza virus hemagglutinin antigen is added to the molten lipids.

In yet another aspect, the present disclosure provides compositions that comprise an influenza virus hemagglutinin antigen and lipid vesicles, wherein the lipid vesicles are comprised of lipids that include a non-ionic surfactant and the compositions are prepared by a method that includes: melting the lipids to produce molten lipids; combining the molten lipids with an aqueous solution that includes the influenza virus hemagglutinin antigen; and homogenizing the resulting product, wherein the molten lipids and aqueous solution are combined in relative amounts and volumes that achieve a lipid concentration of at least about 10 mg/ml (or any one of the other lipid concentration ranges) in the resulting product. In certain embodiments, molten lipids and aqueous solution are combined in relative amounts and volumes that achieve both the desired lipid:antigen weight ratio (e.g., at least about 50:1 or any one of the aforementioned ranges) and a lipid concentration of at least about 10 mg/ml (or any one of the other lipid concentration ranges) in the resulting product. In certain embodiments, the lipid content is also at least about 5 mg per unit dose (or any one of the other lipid content ranges). In certain embodiments, molten lipids are added to the aqueous solution that includes the influenza virus hemagglutinin antigen. In certain embodiments, aqueous solution that includes the influenza virus hemagglutinin antigen is added to the molten lipids.

In certain embodiments, influenza virus hemagglutinin antigen is from an influenza A H1N1 strain. In certain embodiments, influenza virus hemagglutinin antigen is from an influenza A H3N2 strain. In certain embodiments, influenza virus hemagglutinin antigen is from an influenza B strain. In certain embodiments, influenza virus hemagglutinin antigen is from two or more of an influenza A H1N1 strain, an influenza A H3N2 strain and an influenza B strain. In certain embodiments, influenza virus hemagglutinin antigen is from an influenza A H1N1 strain, an influenza A H3N2 strain and an influenza B strain. In certain embodiments, provided compositions comprise approximately equal amounts of influenza virus hemagglutinin antigen from each strain.

In certain embodiments, provided compositions comprise one or more inactivated influenza viruses that include influenza virus hemagglutinin antigen. In certain embodiments, provided compositions comprise one or more attenuated influenza viruses that include influenza virus hemagglutinin antigen. In certain embodiments, influenza virus hemagglutinin antigen is present as a split virus antigen. In certain embodiments, influenza virus hemagglutinin antigen is present as a subunit antigen. In certain embodiments, at least a portion of the influenza virus hemagglutinin antigen is associated with lipid vesicles. In certain embodiments, at least a portion of the influenza virus hemagglutinin antigen is entrapped within lipid vesicles.

In certain embodiments, provided compositions further comprise an adjuvant. In certain embodiments, provided compositions comprise a TLR-4 agonist adjuvant. In certain embodiments, provided compositions comprise an attenuated lipid A derivative. In certain embodiments, provided compositions comprise a monophosphoryl derivative of lipid A. In certain embodiments, provided compositions comprise a 3-deacyl monophosphoryl derivative of lipid A. In certain embodiments, at least a portion of TLR-4 agonist adjuvant is associated with lipid vesicles. In certain embodiments, TLR-4 agonist adjuvant is co-melted with lipids during preparation of provided compositions. In certain embodiments, TLR-4 agonist adjuvant is combined with molten lipids and aqueous solution that includes influenza virus hemagglutinin antigen during preparation of provided compositions (e.g., by mixing with the aqueous solution that includes influenza virus hemagglutinin antigen before it is combined with molten lipids). In certain embodiments, TLR-4 agonist adjuvant is added prior to drying (e.g., lyophilization) of provided compositions.

In certain embodiments, provided compositions are prepared by a method that does not involve storing them under temperature-controlled conditions. In certain embodiments, provided compositions are prepared by a method that involves storing them at a temperature that at least temporarily exceeds 8° C., 15° C., 20° C., 25° C., 30° C. or 35° C.

In certain embodiments, provided compositions are prepared by a method that involves storing them in dried (e.g., lyophilized) form.

In another aspect, the present disclosure provides methods of treating a subject suffering from, or at risk for, an influenza infection by providing one of the aforementioned compositions in dried (e.g., lyophilized) form; rehydrating the composition; and administering to the subject a therapeutically effective amount of the rehydrated composition. In certain embodiments, rehydrated compositions are administered by intramuscular injection.

In yet another aspect, the present disclosure provides methods of preparing compositions that comprise an influenza virus hemagglutinin antigen and lipid vesicles, wherein the lipid vesicles are comprised of lipids that include a non-ionic surfactant, the method comprising: melting the lipids to produce molten lipids; combining the molten lipids with an aqueous solution that includes the influenza virus hemagglutinin antigen; and homogenizing the resulting product, wherein the molten lipids and aqueous solution are combined in relative amounts that achieve the desired lipid:antigen weight ratio (e.g., at least about 50:1 or any one of the aforementioned ranges) in the resulting product. In certain embodiments, molten lipids are added to the aqueous solution that includes the influenza virus hemagglutinin antigen. In certain embodiments, aqueous solution that includes the influenza virus hemagglutinin antigen is added to the molten lipids.

In yet another aspect, the present disclosure provides methods of preparing compositions that comprise an influenza virus hemagglutinin antigen and lipid vesicles, wherein the lipid vesicles are comprised of lipids that include a non-ionic surfactant, the method comprising: melting the lipids to produce molten lipids; combining the molten lipids with an aqueous solution that includes the influenza virus hemagglutinin antigen; and homogenizing the resulting product, wherein the molten lipids and aqueous solution are combined in relative amounts and volumes that achieve a lipid concentration of at least about 10 mg/ml (or any one of the other lipid concentration ranges) in the resulting product. In certain embodiments, molten lipids and aqueous solution are combined in relative amounts and volumes that achieve both the desired lipid:antigen weight ratio (e.g., at least about 50:1 or any one of the aforementioned ranges) and a lipid concentration of at least about 10 mg/ml (or any one of the other lipid concentration ranges) in the resulting product. In certain embodiments, molten lipids are added to the aqueous solution that includes the influenza virus hemagglutinin antigen. In certain embodiments, aqueous solution that includes the influenza virus hemagglutinin antigen is added to the molten lipids.

BRIEF DESCRIPTION OF THE DRAWING

FIG. 6 shows the potency against H1N1 virus and H3N2 virus of an exemplary licensed influenza vaccine in mice (dose-sparing at 1/30× standard human unit dose) either formulated with NISV or not formulated with NISV with the exemplary TLR-4 agonist adjuvant PHAD compared to the licensed influenza vaccine (dose-equivalent at 0.1× standard human unit dose) without formulation into NISV or adjuvant as described in Example 4, Table 6. All compositions were stored at 4° C. and 40° C. for 6 months and then injected into mice IM and sera were tested 15 days after the second immunization. The results are presented as HAI titers against H1N1 or H3N2.

Figure 11A:
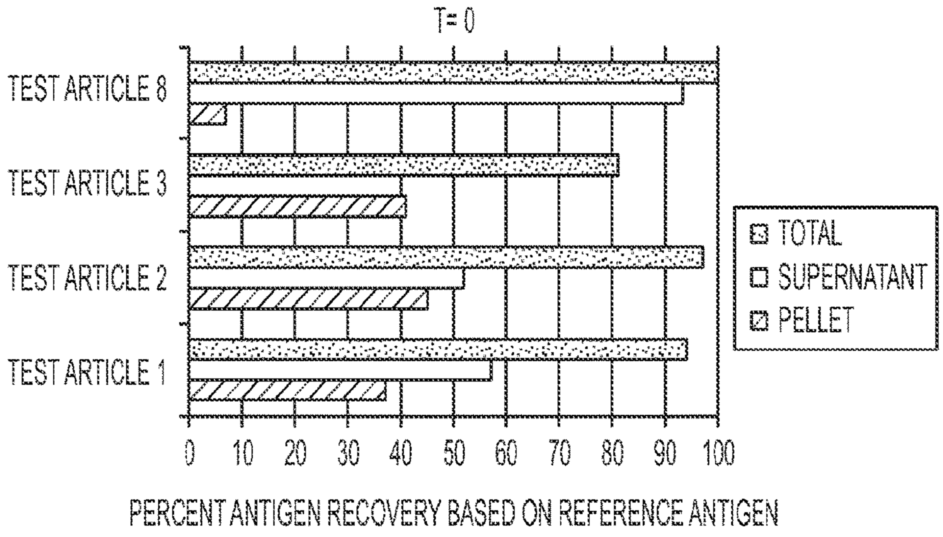
Figure 11B:
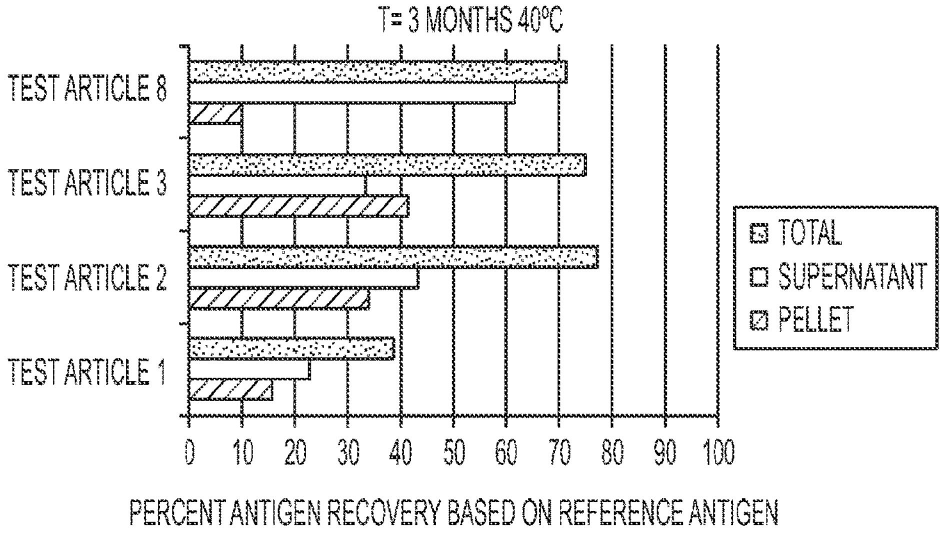

FIG. 11 shows in vitro HA antigen content for unformulated commercial Fluzone® (Test article 8) versus a 300:1 lipid:antigen ratio NISV Fluzone® composition (Test article 3), a 100:1 lipid:antigen ratio NISV Fluzone® composition (Test article 2) and a 30:1 lipid:antigen ratio NISV Fluzone® composition (Test article 1). Aliquots of reconstituted samples were analysed by sELISA to determine antigen content (or "in vitro potency") for the four compositions at (A) T=0 and (B) T=3 months at 40° C.

Figure 12A:
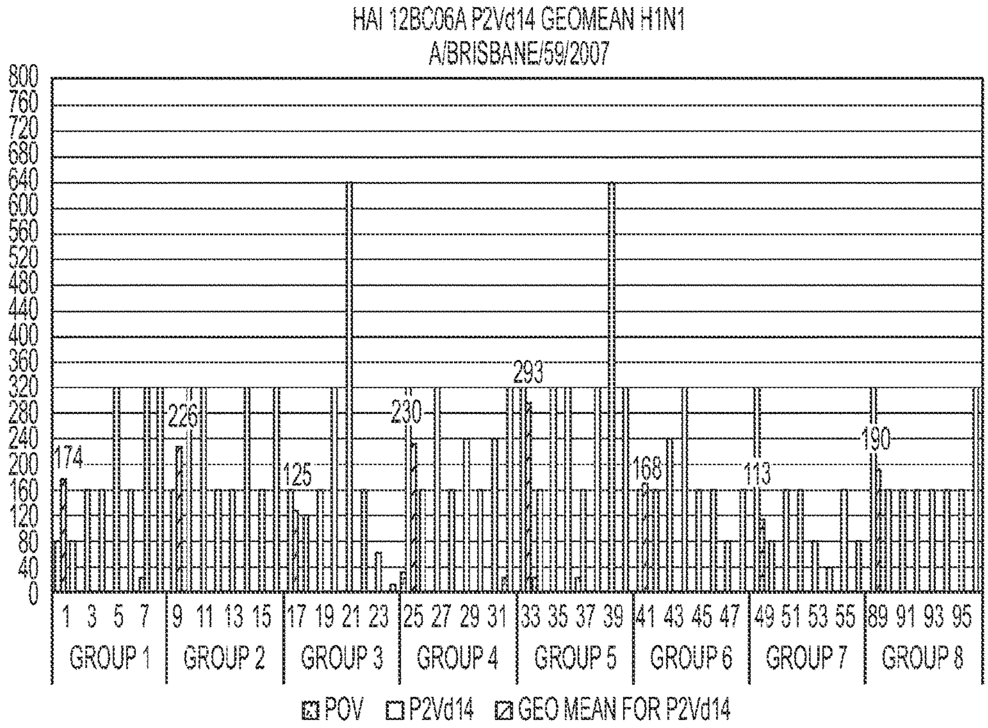
Figure 12B:
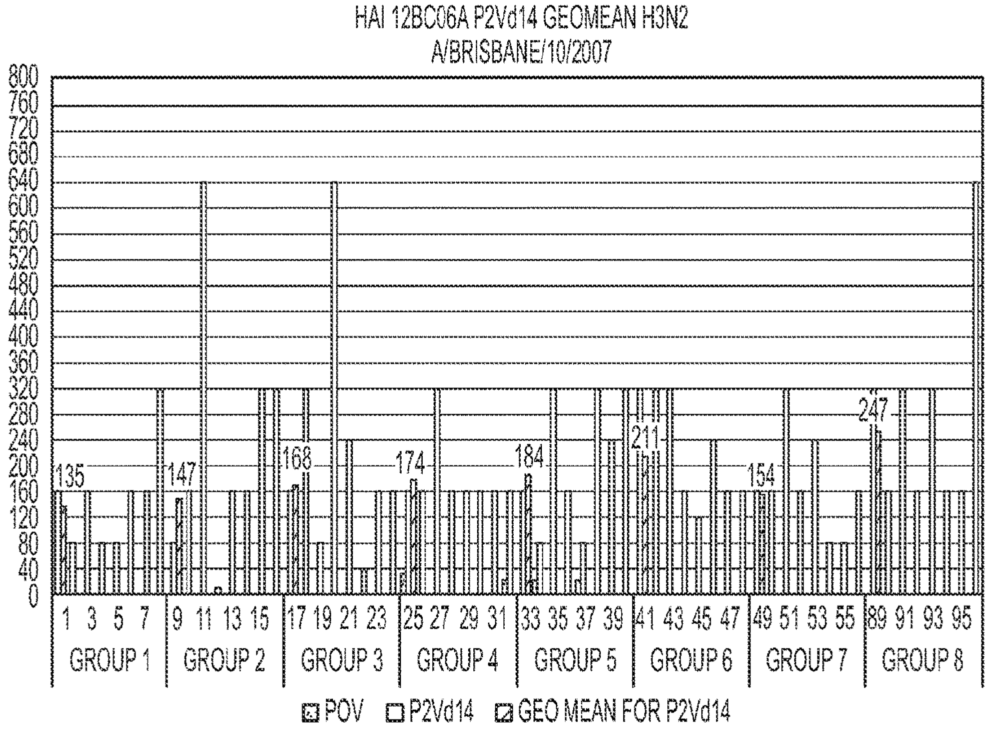

FIG. 12 shows the potency against (A) H1N1 virus and (B) H3N2 virus of various NISV Fluzone® compositions at different lipid:antigen ratios, lipid concentrations and lipid contents as described in Example 7. The compositions at T=0 were injected into mice IM and sera were tested 15 days after the second immunization. The results are presented as individual HAI titers against H1N1 and H3N2 and the geometric mean(s) for the same data set(s).

Figure 13A:
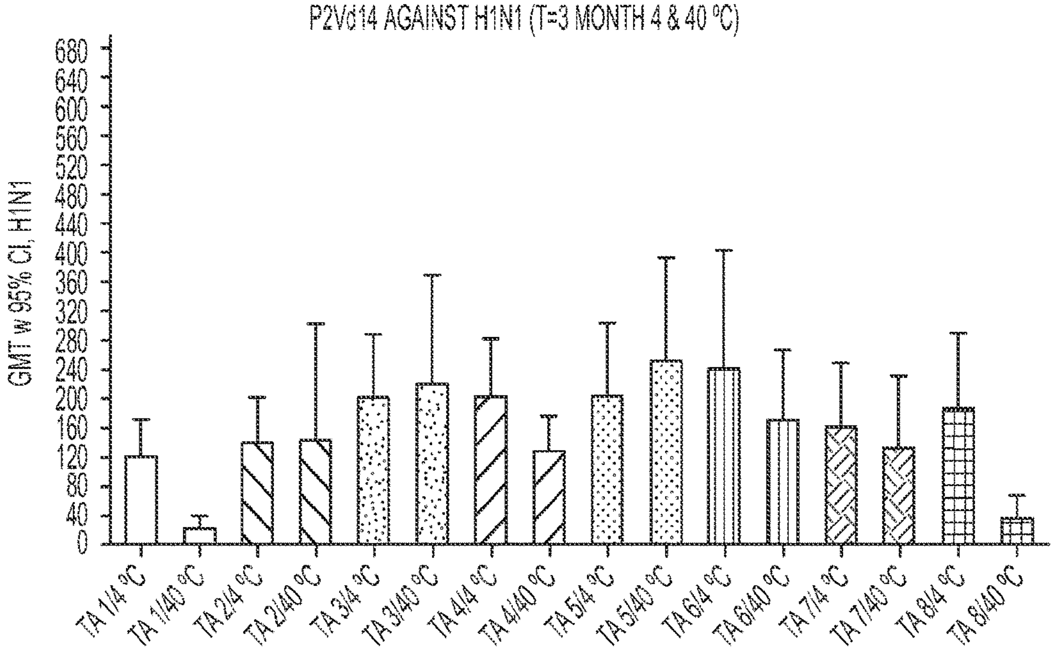
Figure 13B:
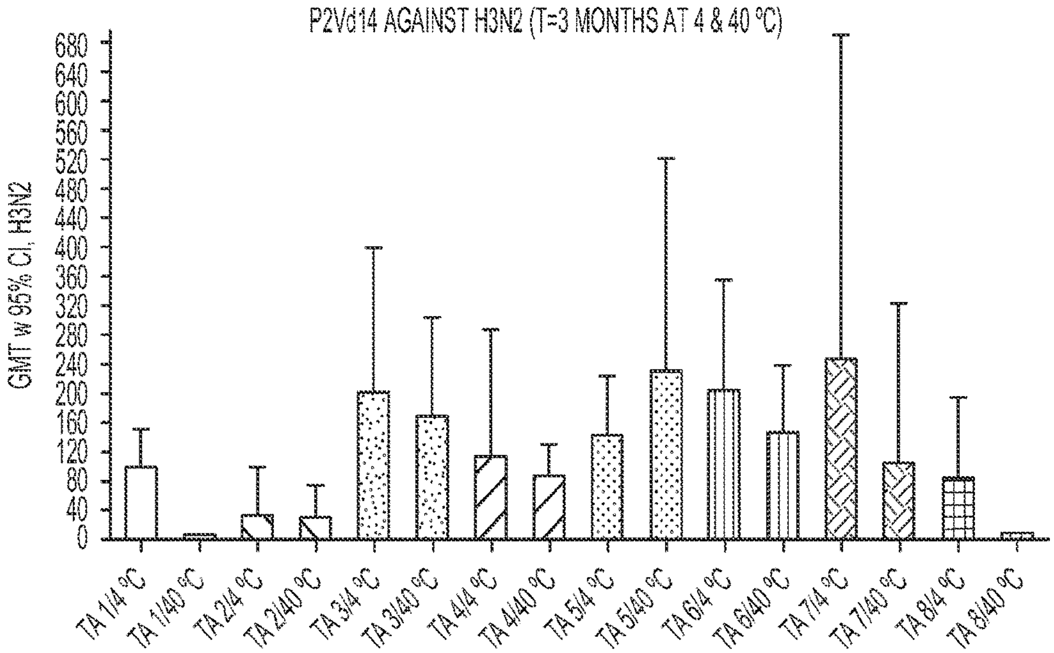

FIG. 13 shows the potency against (A) H1N1 virus and (B) H3N2 virus of various NISV Fluzone® compositions at different lipid:antigen ratios and different lipid concentrations (during homogenization and/or reconstitution) as described in Example 7. All compositions were stored at 4° C. and 40° C. for 3 months and then injected into mice IM and sera were tested 15 days after the second immunization. The results are presented as the geometric mean of HAI titers against H1N1 and H3N2.

DEFINITIONS

Throughout the present disclosure, several terms are employed that are defined in the following paragraphs.

As used herein, the term "antigen" refers to a substance containing one or more epitopes (either linear, conformational or both) that is/are recognized by an antibody. In some embodiments, the antibody is a human antibody, in some embodiments, raised in a human organism exposed to the antigen, in some embodiments where such exposure occurs by or includes exposure in the bloodstream. In certain embodiments, an antigen may be an "immunogen."

As used herein, the term "immune response" refers to a response elicited in a host animal. An immune response may refer to cellular immunity, humoral immunity or may involve both. An immune response may be limited to a part of the immune system. For example, in certain embodiments, an increased IFNγ response is considered to be an immune response. In certain embodiments, a mucosal IgA response (e.g., as measured in nasal and/or rectal washes) is considered to be an immune response. In certain embodiments, a systemic IgG response (e.g., as measured in serum) is considered to be an immune response. In certain embodiments, production, by the host animal, of antibodies that inhibit hemagglutination, e.g., as measured in a Hemagglutination Inhibition (HAI) assay is considered to be an immune response.

As used herein, the term "immunogenic" is used to refer to a substance that produces an immune response in a host animal against a non-host entity (e.g., an influenza virus). In certain embodiments, this immune response forms the basis of the protective immunity elicited by a vaccine against a specific infectious organism (e.g., an influenza virus). In certain embodiments, an immunogenic substance produces an immune response in humans. In certain embodiments, an immunogenic substance produces an immune response when contacted with the bloodstream of a body, for example of a human body.

As used herein, the term "therapeutically effective amount" refers to an amount sufficient to show a meaningful benefit in a subject being treated, when administered as part of a therapeutic dosing regimen. Those of ordinary skill in the art will appreciate that, in some embodiments, a particular composition may be considered to contain a therapeutically effective amount if it contains an amount appropriate for a unit dosage form administered in a therapeutic dosing regimen, even though such amount may be insufficient to achieve the meaningful benefit if administered as a single unit dose. Those of ordinary skill will further appreciate that a therapeutically effective amount of an immunogenic composition may differ for different subjects receiving the composition, for example depending on such factors as the desired biological endpoint, the nature of the composition, the route of administration, the health, size and/or age of the subject being treated, etc. In some embodiments, a therapeutically effective amount is one that has been correlated with beneficial effect when administered as part of a particular therapeutic dosing regimen (e.g., a single administration or a series of administrations such as in a traditional "boosting" regimen). In some embodiments, a therapeutically effective amount is one that has been approved by a therapeutic licensing body (e.g., the Food and Drug Administration or the European Medicines Agency) as part of a particular therapeutic dosing regimen (e.g., see the package inserts for various licensed influenza vaccines as set forth by the Food and Drug Administration at www.fda.gov/BiologicsBloodVaccines/Vaccines/ApprovedProducts/ucm181950.htm for licensed monovalent vaccines and www.fda.gov/BiologicsBloodVaccines/Vaccines/ApprovedProducts/ucm094045.htm for licensed trivalent vaccines).

As used herein, the term "treat" (or "treating", "treated", "treatment", etc.) refers to the administration of provided compositions to a subject who is suffering from or susceptible to a disease, a symptom of a disease or a predisposition toward a disease, with the purpose to alleviate, relieve, alter, ameliorate, improve or affect the disease, a symptom or symptoms of the disease, or the predisposition toward the disease. In certain embodiments, the term "treating" refers to vaccination of a subject. In general, treatment can achieve reduction in severity and/or frequency of one or more symptoms or characteristics of the disease, and/or can delay onset of one or more such symptoms or characteristics.

DETAILED DESCRIPTION OF CERTAIN EMBODIMENTS

All vaccines lose potency over time and the rate of potency loss is temperature-dependent. Therefore, cold-chain systems have been established to ensure that the potency of vaccines is maintained by storing them under refrigerated conditions (in most cases between 2 and 8° C.) until the point of use. Establishing a cold-chain for vaccine storage and distribution is a major undertaking and maintenance is difficult. It is also apparent that, despite best efforts, cold-chains do not always function as intended for many reasons, such as improperly maintained or outdated refrigeration equipment, power outages resulting in equipment failure, poor compliance with cold-chain procedures and inadequate monitoring. The result is that vaccines in the cold-chain are often subjected to temperature excursions (i.e., temperatures outside of the target range).

For current influenza trivalent vaccines on the market which are predominantly available in a liquid composition, it is important to understand the importance of cold-chain requirements and proper vaccine management in order to ensure that subjects are receiving a stable and potent influenza vaccine. If influenza vaccines are not maintained properly (e.g., not kept within the required temperature range of 2 to 8° C.), the vaccine can become unstable and this in turn has a significant impact on potency which can result in the vaccinated subject not converting serologically post immunization. The vaccinated subjects believe that they are protected because they have been immunized when in fact they remain vulnerable to influenza infection because the vaccine is not potent due to instability resulting from temperature excursions.

The present disclosure provides compositions and methods for treating influenza that solve some of these challenges. As described herein, provided compositions and methods are based on the development of certain compositions that include an influenza virus hemagglutinin antigen in combination with lipid vesicles that include a non-ionic surfactant (NISVs) and optionally an adjuvant. In certain embodiments, provided compositions remain potent even when they are not stored in a standard cold-chain system (i.e., they are thermostable).

I. Influenza Virus Hemagglutinin Antigen

In general, compositions of the present disclosure include an influenza virus hemagglutinin antigen. Hemagglutinin antigen utilized in accordance with the present invention is not limited to full length wild-type hemagglutinin antigens and, as used herein, the term "hemagglutinin antigen" therefore also encompasses immunogenic fragments and variants of full length wild-type hemagglutinin antigens. The term "hemagglutinin antigen" also encompasses fusion proteins and conjugates that include any of the foregoing. The amount of hemagglutinin antigen in provided compositions may be determined by any known method in the art. In some embodiments, the amount of hemagglutinin antigen may be determined by an ELISA (e.g., one or more sub-type specific sELISAs). This approach is commonly used to standardize the amount of antigen in split virus vaccines.

There are no restrictions on the type of hemagglutinin antigen used. In particular, hemagglutinin antigen may be taken from a single influenza virus strain or a combination of influenza virus strains. As described above, current influenza vaccines are usually "trivalent" vaccines that contain antigens derived from two influenza A virus strains (e.g., H1N1 and H3N2) and one influenza B strain. Thus, in certain embodiments, a trivalent composition of the present disclosure may include hemagglutinin antigen from an influenza A H1N1 strain, an influenza A H3N2 strain and an influenza B strain. Certain trivalent compositions may comprise approximately equal amounts of hemagglutinin antigen from each of these strains.

Monovalent vaccines are also known in the art and encompassed by the present invention. In some embodiments, provided compositions are monovalent. Monovalent vaccines are often considered to be particularly useful for example in a pandemic situation. A monovalent, pandemic influenza vaccine will most likely contain hemagglutinin antigen from a single A strain. In some embodiments, hemagglutinin antigen for use in a monovalent composition will be derived from a pandemic influenza strain. For example, in some embodiments, hemagglutinin antigen for use in a monovalent composition is from an influenza A (H1N1 of swine origin) strain. As demonstrated in the Examples, compositions that include hemagglutinin antigen from an influenza A H3N2 strain (alone or in combination with other antigens) are of particular interest because antigens from this strain appear to be particularly sensitive to high temperatures.

There are also no restrictions on the source of hemagglutinin antigen used (i.e., native, recombinant, synthetic, etc.). Predominantly three types of vaccines are used worldwide to protect against influenza: whole virus vaccines, split virus vaccines containing external and internal components of the virus, and subunit vaccines composed of just external components of the virus (hemagglutinin and neuraminidase).

In certain embodiments, compositions of the present invention comprise one or more whole viruses that include hemagglutinin antigen. In certain embodiments, influenza viruses are inactivated. It will be appreciated that any method may be used to prepare an inactivated influenza virus. WO 09/029,695 describes exemplary methods for producing a whole inactivated virus vaccine. In general, these methods will involve propagating an influenza virus in a host cell, optionally lysing the host cell to release the virus, isolating and then inactivating the virus. Chemical treatment (e.g., formalin, formaldehyde, among others) is commonly used to inactivate viruses for vaccine preparation. However, it is to be understood that other techniques could be used, e.g., treatment with chlorine, exposure to high temperatures, etc. In these treatments the outer virion coat is typically left intact while the replicative function is impaired. In certain embodiments, influenza viruses are attenuated. As is well known in the art, one advantage of a vaccine prepared with an attenuated virus lies in the potential for higher immunogenicity which results from its ability to replicate in vivo without causing a full infection. Live virus vaccines that are prepared from attenuated strains preferably lack pathogenicity but are still able to replicate in the host. One method which has been used in the art to prepare attenuated influenza viruses is viral adaptation which involves serially passing a viral strain through multiple cell cultures. Over time the strain mutates and attenuated strains can then be identified. In certain embodiments the virus may be passed through different cell cultures. In certain embodiments it may prove advantageous to perform one or more of the cell culture steps at a reduced temperature.

In certain embodiments, influenza virus hemagglutinin antigens utilized in accordance with the present invention are based on split virus vaccine technology. Split virus vaccines typically contain a higher concentration of the most immunogenic portions of the virus (e.g., hemagglutinin and neuramidase), while lowering the concentration of less immunogenic viral proteins as well as non-viral proteins present from eggs (used to produce virus) or extraneous agents (e.g., avian leukosis virus, other microorganisms and cellular debris). Generally, split virus vaccines are prepared by a physical process that involves disrupting the virus particle, typically with an organic solvent or a detergent (e.g., Triton X-100), and separating or purifying the viral proteins to varying extents, such as by centrifugation over a sucrose gradient or passage of allantoic fluid over a chromatographic column. In some embodiments, disruption and separation of virus particles is followed by dialysis or ultrafiltration. Methods of viral splitting as well as suitable splitting agents are known in the art (see for example U.S. Patent Publication No. 20090155309).

In certain embodiments, influenza virus hemagglutinin antigens utilized in accordance with the present invention are based on subunit vaccine technology. Generally, subunit vaccines contain only those parts of the influenza virus that are needed for effective vaccination (e.g., eliciting a protective immune response). In some embodiments, subunit influenza antigens are prepared from virus particles (e.g., purification of particular components of the virus). In some embodiments, subunit influenza antigens are prepared by recombinant methods (e.g., expression in cell culture). For example, U.S. Pat. No. 5,858,368 describes methods of preparing a recombinant influenza vaccine using DNA technology. The resulting trivalent influenza vaccine is based on a mixture of recombinant hemagglutinin antigens cloned from influenza virus strains having epidemic potential. The recombinant hemagglutinin antigens are full length, uncleaved, glycoproteins produced from baculovirus expression vectors in cultured insect cells and purified under non-denaturing conditions. In some embodiments, subunit antigens are generated by synthetic methods (e.g., peptide synthesis). Subunit vaccines may also contain purified hemagglutinin antigens prepared from selected strains determined by the WHO.

In certain embodiments, hemagglutinin antigens may be sourced from one or more licensed influenza vaccines. In certain embodiments, hemagglutinin antigen (optionally with other antigens, e.g., neuraminidase antigen) may be purified from the licensed influenza vaccine and then utilized in provided compositions. In certain embodiments, a licensed influenza vaccine may be used "as is" without any purification. Table 1 is a non-limiting list of licensed influenza vaccines. Full prescribing information and details regarding these licensed vaccines can be obtained from the package inserts that are provided with the vaccines themselves, from the manufacturers or suppliers, and/or from the Food and Drug Administration (e.g., see www.fda.gov/BiologicsBloodVaccinesNaccines/ApprovedProducts/ucm181950.htm for licensed monovalent vaccines and www.fda.gov/BiologicsBloodVaccines/Vaccines/ApprovedProducts/ucm094045.htm for licensed trivalent vaccines). The contents of these package inserts are incorporated herein by reference in their entirety.

TABLE 1

| Vaccine | Disease |
|---|---|
| Influenza (Afluria ®) | Seasonal influenza |
| Influenza (Agriflu ®) | Seasonal influenza |
| Influenza (Begrivac ®) | Seasonal influenza |
| Influenza (Enzira ®) | Seasonal influenza |
| Influenza (Fluad ®) | Seasonal influenza |
| Influenza (Fluarix ®) | Seasonal influenza |
| Influenza (FluLaval ®) | Seasonal influenza |
| Influenza (FluMist ®) | Seasonal influenza |
| Influenza (Fluvax ®) | Seasonal influenza |
| Influenza (Fluviral, Fluviral S/F ®) | Seasonal influenza |
| Influenza (Fluvirin ®) | Seasonal influenza |
| Influenza (Fluzone ®) | Seasonal influenza |
| Influenza (Grippol ®) | Seasonal influenza |
| Influenza (Inflexal, Inflexal S, Inflexal V ®) | Seasonal influenza |
| Influenza (Influvac ®) | Seasonal influenza |
| Influenza (Mastaflu ®) | Seasonal influenza |
| Influenza (Mutagrip ®) | Seasonal influenza |
| Influenza (Optaflu ®) | Seasonal influenza |
| Influenza (Vaxigrip ®) | Seasonal influenza |
| H1N1 pandemic influenza (Arepanrix ®) | H1N1 pandemic influenza |
| H1N1 pandemic influenza (Calvapan ®) | H1N1 pandemic influenza |
| H1N1 pandemic influenza (Focetria ®) | H1N1 pandemic influenza |
| H1N1 pandemic influenza (Influenza A (H1N1) 2009 Monovalent Vaccine ®) | H1N1 pandemic influenza |
| H1N1 pandemic influenza (Pandemrix ®) | H1N1 pandemic influenza |

In the following sections we discuss these and other exemplary influenza antigens that could be used in compositions and methods of the present disclosure.

Fluzone®, an inactivated trivalent split influenza vaccine, is developed and manufactured by Sanofi Pasteur, Inc. and may be used in accordance with the present disclosure. Fluzone® contains a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a non-ionic surfactant, octoxinol-9, (Triton® X-100) producing a split viral antigen. The split virus is then further purified by chemical means and suspended in sodium phosphate-buffered isotonic sodium chloride solution. Fluzone® vaccine is then standardized according to requirements for the influenza season and is formulated to contain 45 μg hemagglutinin antigen (HA) per 0.5 ml unit dose, in the recommended ratio of 15 μg HA each, representative of the three prototype strains (e.g., 2007-2008 vaccine was prepared with HA from the A/Solomon Islands/3/2006 (H1N1), A/Wisconsin/67/2005 (H3N2) and B/Malaysia/2506/2004 strains). Fluzone® is formulated for intramuscular (IM) injection.

Another example of a licensed influenza vaccine that may be used in accordance with the present disclosure is Vaxigrip®, which is an inactivated trivalent split influenza vaccine also developed and manufactured by Sanofi Pasteur, Inc. Vaxigrip® is prepared in a similar fashion to the process outlined above for Fluzone® and is similarly formulated for intramuscular injection.

Yet another example of a licensed influenza vaccine that may be used in accordance with the present disclosure is Flumist®. Flumist® is a live, attenuated trivalent vaccine for administration by intranasal spray. The influenza virus strains in Flumist® have three genetic mutations that lead to temperature restricted growth and an attenuated phenotype. The cumulative effect of the antigenic properties and the genetically modified influenza viruses is that they are able to replicate in the nasopharynx to induce protective immunity. In order to produce Flumist®, specific pathogen-free (SPF) eggs are inoculated with each of the appropriate viral strains and incubated to allow vaccine virus replication. The allantoic fluid of these eggs is harvested, pooled and then clarified by filtration. The virus is concentrated by ultracentrifugation and diluted with stabilizing buffer to obtain the final sucrose and potassium phosphate concentrations. Viral harvests are then sterile filtered to produce the monovalent bulks. Monovalent bulks from the three strains are subsequently blended and diluted as required to attain the desired potency with stabilizing buffers to produce the trivalent bulk vaccine. The bulk vaccine is then filled directly into individual sprayers for nasal administration. Each pre-filled refrigerated Flumist® sprayer contains a single 0.2 ml unit dose. Each 0.2 ml unit dose contains $10^{6.5-7.5}$ FFU of live attenuated influenza virus reassortants of each of the appropriate three viral strains.

As described above, several influenza vaccines are currently licensed. It is to be understood that any one or combination of these licensed influenza vaccines may be combined with lipid vesicles as described herein. For example, commercial Fluzone® may be combined in this manner to produce a composition. In some embodiments, licensed influenza vaccines are first purified (e.g., to remove adjuvant or other reagents in the vaccine). In some embodiments, licensed influenza vaccines are not purified (i.e., they are used "as is") prior to formulation with lipid vesicles as described herein.

II. Adjuvants

Compositions of the present disclosure may include an adjuvant. As is well known in the art, adjuvants are agents that enhance immune responses (e.g., see "Vaccine Design: The Subunit and Adjuvant Approach", Pharmaceutical Biotechnology, Volume 6, Eds. Powell and Newman, Plenum Press, New York and London, 1995).

Toll-like receptors (TLRs) are a family of proteins homologous to the Drosophila Toll receptor, which recognize molecular patterns associated with pathogens and thus aid the body in distinguishing between self and non-self molecules. Substances common in viral pathogens are recognized by TLRs as pathogen-associated molecular patterns. For example, without limitation, TLR-4 is thought to recognize patterns in lipopolysaccharides (TLR-4 has also been designated as CD284 or cluster of differentiation 284); while TLR-7/8 are thought to recognize single-stranded RNAs and small synthetic molecules; and TLR-9 is thought to recognize unmethylated bacterial DNA or synthetic oligonucleotides. When a TLR is triggered by such pattern recognition, a series of signaling events occurs that leads to inflammation and activation of innate and adaptive immune responses.

In some embodiments, provided compositions include a TLR-4 agonist adjuvant. A number of synthetic ligands containing the molecular patterns recognized by TLR-4 (TLR-4 agonists) have been developed as adjuvants and may be included in provided compositions. Attenuated lipid A derivatives (ALD) such as monophosphoryl lipid A (MPL) and 3-deacyl monophosphoryl lipid A (3D-MPL) are exemplary adjuvants that are agonists for TLR-4. ALDs are lipid A-like molecules that have been altered or constructed to reduce or modify the adverse effects of lipid A. These adverse effects include pyrogenicity, local Shwarzman reactivity and toxicity as evaluated in the chick embryo 50% lethal dose assay ($CELD_{50}$). MPL and 3D-MPL are described in U.S. Pat. Nos. 4,436,727 and 4,912,094, respectively. MPL was originally derived from lipid A, a component of enterobacterial lipopolysaccharides (LPS), a potent but highly toxic immune system modulator. Exemplary synthetic derivatives of MPL are described in PCT Publication No. WO95/14026 and also US Patent Publication Nos. 20080131466 and 20090181078. 3D-MPL differs from MPL in that the acyl residue that is ester linked to the reducing-end glucosamine at position 3 has been selectively removed (e.g., see U.S. Pat. Nos. 4,877,611; 4,866,034 and 4,912,094). It will be appreciated that MPL, 3D-MPL and their derivatives may include a mixture of a number of fatty acid substitution patterns, i.e., heptaacyl, hexaacyl, pentaacyl, etc., with varying fatty acid chain lengths. Thus, various forms of MPL and 3D-MPL, including mixtures thereof, are encompassed by the present disclosure.

Figure 1:
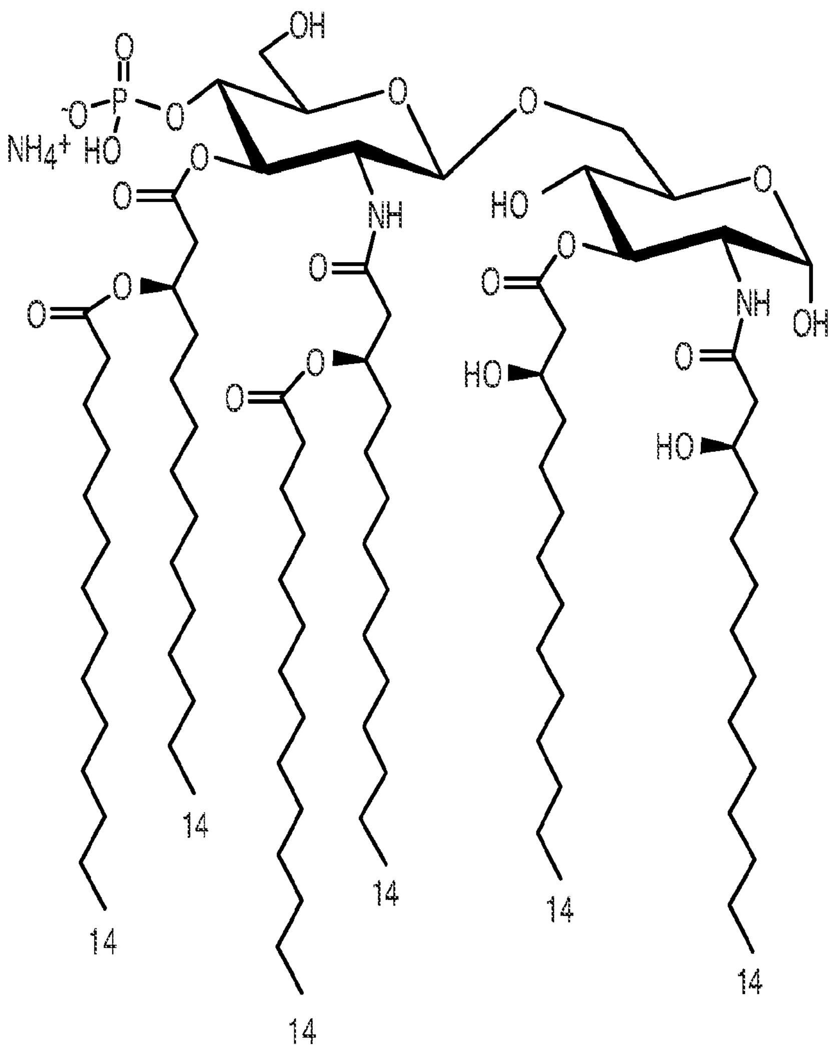
FIG. 1 shows the chemical structure of the exemplary TLR-4 agonist adjuvant phosphorylated hexaacyl disaccharide (ammonium salt) or PHAD (from Avanti Polar Lipids, Inc. of Alabaster, Ala.).
Figure 2:
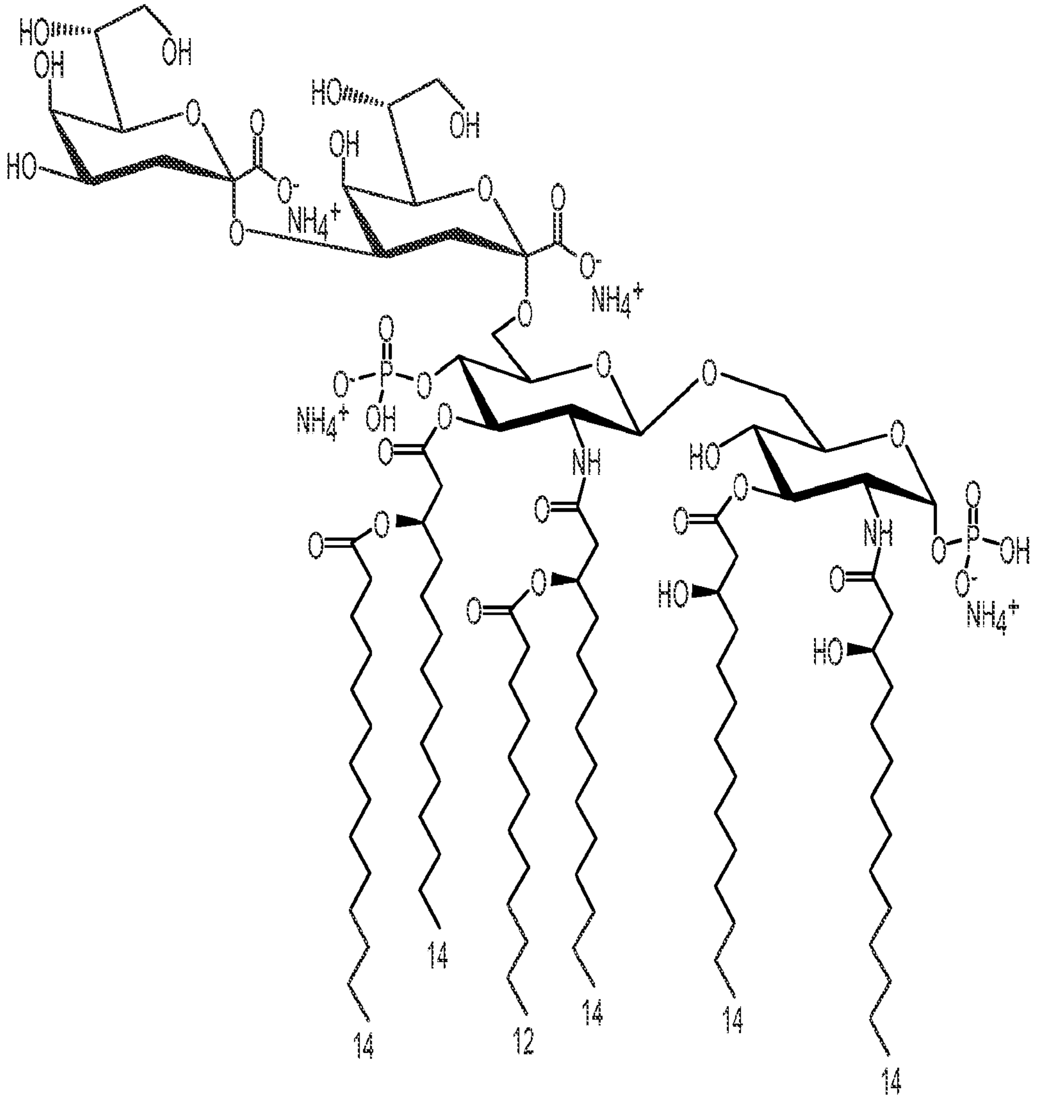
FIG. 2 shows the chemical structure of another exemplary TLR-4 agonist adjuvant di[3-deoxy-D-manno-octulosonyl]-lipid A (ammonium salt) (from Avanti Polar Lipids, Inc. of Alabaster, Ala.).

MPL is available from Avanti Polar Lipids, Inc. of Alabaster, Ala. as PHAD or phosphorylated hexaacyl disaccharide (ammonium salt). FIG. 1 shows a chemical structure of PHAD. The structure of di[3-deoxy-D-manno-octulosonyl]-lipid A (ammonium salt) another exemplary TLR-4 agonist adjuvant is shown in FIG. 2 (also from Avanti Polar Lipids, Inc. of Alabaster, Ala.). In some embodiments these or other ALDs may be combined with trehalosedimycolate (TDM) and cell wall skeleton (CWS), e.g., in a 2% squalene/Tween™ 80 emulsion (e.g., see GB Patent No. 2122204).

Those skilled in the art are able to identify other suitable TLR-4 agonist adjuvants. For example, alkyl glucosaminide phosphates (AGPs) such as those disclosed in PCT Publication No. WO98/50399 or U.S. Pat. Nos. 6,303,347 and 6,764,840 may be used. Other suitable TLR-4 agonists are described in PCT Publication No. WO03/011223 and WO03/099195 (e.g., compounds I-III disclosed on pages 4-5 of WO03/011223 or on pages 3-4 of WO03/099195 and in particular those compounds disclosed in WO03/011223 as ER803022, ER803058, ER803732, ER804053, ER804057, ER804058, ER804059, ER804442, ER804680, and ER804764).

In some embodiments, provided compositions include between about 1 and 50 µg of a TLR-4 agonist adjuvant. In certain embodiments, provided compositions include between about 1-40, 1-30, 1-20, 1-10 or 1-5 µg of a TLR-4 agonist adjuvant. In certain embodiments, provided compositions include between about 10-40, 10-30, or 10-20 µg of a TLR-4 agonist adjuvant. In certain embodiments, provided compositions include between about 1-2, 1-3, 1-4, 1-5, 1-6, 1-7, 1-8, 1-9 or 1-10 µg of a TLR-4 agonist adjuvant. In certain embodiments, provided compositions include between about 5-20, 5-18, 5-16, 5-14, 5-12, 5-10, 5-9, 5-8 or 5-7 µg of a TLR-4 agonist adjuvant.

In some embodiments, provided compositions include a TLR-7/8 agonist adjuvant. A number of synthetic ligands containing the molecular patterns recognized by TLR-7/8 (TLR-7/8 agonists) have been developed as adjuvants and may be included in provided compositions. Exemplary TLR-7/8 ligands include, but are not limited to CL075 (a thiazoloquinolone derivative), CL097 (a highly water-soluble imidazoquinoline compound), and R848 (a low molecular weight synthetic imidazoquinoline compound), each of which is available from InvivoGen of San Diego, Calif. In some cases, poly(dT), a thymidine homopolymer phosphorothioate oligodeoxynucleotide, may be used in combination with an imidazoquinoline to increase TLR-8 mediated signaling and/or to decrease TLR-7 mediated signaling (e.g., see Jurk et al., *Eur J. Immunol.* 36(7):1815-26, 2006). Those skilled in the art are able to identify suitable amounts and/or derivatives of TLR-7/8 agonist adjuvants for use in accordance with the present invention.

In some embodiments, provided compositions include a TLR-9 agonist adjuvant. In general, bacterial DNA is rich in unmethylated 2'-deoxyribo(cytidine-phosphateguanosine) (CpG) dinucleotides, in contrast to mammalian DNA, which typically contains a low frequency of CpG dinucleotides that are mostly methylated. Unmethylated CpGs in particular base contexts, called CpG motifs, have been shown to activate the immune system via TLR-9. In some cases, TLR-9 recognition of CpG DNA leads to production of proinflammatory cytokines (e.g., IL-6, IL-12). CpG motifs may contain a conserved core sequence that leads to high levels of stimulation of a TLR-9 in a particular species. For example, GACGTT has been shown to highly stimulate mouse TLR-9, whereas CpG motifs containing more than one CpG and the core sequence GTCGTT have been shown to stimulate human TLR-9. A number of synthetic ligands containing the molecular patterns recognized by TLR-9 (TLR-9 agonists) have been developed as adjuvants and may be included in provided compositions. Those skilled in the art are able to identify suitable amounts and/or derivatives of TLR-9 agonist adjuvants for use in accordance with the present invention.

In certain embodiments, at least a portion of adjuvant is associated with lipid vesicles. In certain embodiments, at least a portion of adjuvant is not associated with lipid vesicles. In certain embodiments, adjuvant is co-melted with lipids during preparation of provided compositions. In certain embodiments, adjuvant is combined with molten lipids and aqueous solution that includes influenza virus hemagglutinin antigen during preparation of provided compositions (e.g., by mixing with the aqueous solution that includes influenza virus hemagglutinin antigen before it is combined with molten lipids). In certain embodiments, adjuvant is added prior to drying (e.g., lyophilization) of provided compositions.

III. Lipid Vesicles

In general, compositions of the present disclosure include lipid vesicles that are comprised of lipids that include a non-ionic surfactant. Such lipid vesicles are also referred to as "non-ionic surfactant vesicles", or "NISVs", herein. As is well known in the art, vesicles generally have an aqueous compartment enclosed by one or more lipid bilayers.

Non-Ionic Surfactant

Any non-ionic surfactant with appropriate amphipathic properties may be used to form vesicles for use in accordance with the present invention. Without limitation, examples of suitable surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$alkanoyl or alkenoyl moiety, for example caproyl, lauroyl, myristoyl, palmitoyl, oleyl or stearoyl. An exemplary ester-linked surfactant is 1-monopalmitoyl glycerol.

Alternatively or additionally, ether-linked surfactants may be used as or included as a non-ionic surfactant in accordance with the present invention. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

Ionic Amphiphile

It is to be understood that lipids used to make lipid vesicles for use in accordance with the present invention may incorporate an ionic amphiphile, e.g., so that vesicles take on a negative charge. For example, this may help to stabilize vesicles and provide effective dispersion.

Without limitation, acidic materials such as higher alkanoic and alkenoic acids (e.g., palmitic acid, oleic acid) or other compounds containing acidic groups including phosphates such as dialkyl phosphates (e.g., dicetylphospate, or phosphatidic acid or phosphatidyl serine) and sulphate monoesters such as higher alkyl sulphates (e.g., cetylsulphate), may all be used for this purpose. The ionic amphiphile, if present, will typically comprise, between 1 and 50% by weight of the non-ionic surfactant (e.g., 1-5%, 1-10%, 1-15%, 1-20, 1-25%, 1-30%, 1-35%, 1-40%, 1-45%, 5-10%, 5-15%, 5-20%, 5-25%, 5-30%, 5-35%, 5-40%, 5-45%, 5-50%, 10-15%, 10-20%, 10-25%, 10-30%, 10-35%, 10-40%, 10-45%, 10-50%, 15-20%, 15-25%, 15-30%, 15-35%, 15-40%, 15-45%, 15-50%, 20-25%, 20-30%, 20-35%, 20-40%, 20-45%, 20-50%, 25-30%, 25-35%, 25-40%, 25-45%, 25-50%, 30-35%, 30-40%, 30-45%, 30-50%, 35-40%, 35-45%, 35-50%, 40-45%, 40-50%, or 45-50%).

Hydrophobic Material

To form vesicles in accordance with the present invention, lipids may also incorporate an appropriate hydrophobic material of higher molecular mass capable of forming a bilayer (such as a steroid, e.g., a sterol such as cholesterol). The presence of such a hydrophobic material of higher molecular mass capable of forming a bilayer (such as a steroid, e.g., a sterol such as cholesterol) assists in forming the bilayer on which the physical properties of the vesicle depend. The material, if present, will typically comprise between 20 and 120% by weight of the non-ionic surfactant (e.g., 20-30%, 20-40%, 20-50%, 20-60%, 20-70%, 20-80%, 20-90%, 20-100%, 20-110%, 30-40%, 30-50%, 30-60%, 30-70%, 30-80%, 30-90%, 30-100%, 30-110%, 30-120%, 40-50%, 40-60%, 40-70%, 40-80%, 40-90%, 40-100%, 40-110%, 40-120%, 50-60%, 50-70%, 50-80%, 50-90%, 50-100%, 50-110%, 50-120%, 60-70%, 60-80%, 60-90%, 60-100%, 60-110%, 60-120%, 70-80%, 70-90%, 70-100%, 70-110%, 70-120%, 80-90%, 80-100%, 80-110%, 80-120%, 90-100%, 90-110%, 90-120%, 100-110%, 100-120%, or 110-120%).

Exemplary Lipid Vesicles

In certain embodiments, lipid vesicles for use in accordance with the present invention comprise a non-ionic surfactant, an ionic amphiphile and a steroid. In certain embodiments, lipid vesicles comprise 1-monopalmitoyl glycerol, dicetylphospate and cholesterol.

In certain embodiments, lipid vesicles for use in accordance with the present invention consist essentially of a non-ionic surfactant, an ionic amphiphile and a steroid. In certain embodiments, lipid vesicles consist essentially of 1-monopalmitoyl glycerol, dicetylphospate and cholesterol.

In certain embodiments, lipid vesicles for use in accordance with the present invention do not comprise or are substantially free of a transport enhancing molecule. In some embodiments, lipid vesicles for use in accordance with the present invention do not comprise or are substantially free of "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, lipid vesicles for use in accordance with the present invention do not comprise or are substantially free of acyloxylated amino acids, such as acylcarnitines and salts thereof, and palmitoylcarnitines.

Lipid: Antigen Weight Ratio

The present invention provides the surprising finding that both immunogenicity and thermostability of provided compositions are controlled at least in part by relative amounts of lipids and hemagglutinin antigen present in the compositions.

For example, through experimentation, we have found that compositions with high lipid content (e.g., a lipid: antigen weight ratio of about 450:1) are far less immunogenic than compositions with a slightly lower lipid content (e.g., a lipid:antigen weight ratio of about 300:1). While compositions with lower lipid content are generally more immunogenic we have also found that they are less thermostable (e.g., at a lipid:antigen weight ratio of about 30:1 we observe very little thermostability). In light of these experimental findings (discussed in more detail in the Examples) we are now able to define and provide new sets of compositions that are both immunogenic and thermostable. In certain embodiments, provided compositions have a lipid:

antigen weight ratio of at least about 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1 or 300:1. In certain embodiments, the lipid:antigen weight ratio is less than about 400:1, 390:1, 380:1, 370:1, 360:1, 350:1, 340:1, 330:1, 320:1 or 310:1. In certain embodiments, the lipid:antigen weight ratio is within a range of about 50:1 to about 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1 or 400:1. In certain embodiments, the lipid:antigen weight ratio is within a range of about 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, or 390:1 to about 400:1. In certain embodiments, the lipid:antigen weight ratio is within a range of about 50:1 to about 100:1, about 50:1 to about 150:1, about 50:1 to about 200:1, about 50:1 to about 250:1, about 50:1 to about 300:1, about 50:1 to about 350:1, or about 50:1 to about 400:1. In certain embodiments, the lipid:antigen weight ratio is within a range of about 100:1 to about 150:1, about 100:1 to about 200:1, about 100:1 to about 250:1, about 100:1 to about 300:1, about 100:1 to about 350:1, or about 100:1 to about 400:1. In certain embodiments, the lipid:antigen weight ratio is within a range of about 150:1 to about 200:1, about 150:1 to about 250:1, about 150:1 to about 300:1, about 150:1 to about 350:1, or about 150:1 to about 400:1. In certain embodiments, the lipid:antigen weight ratio is within a range of about 200:1 to about 250:1, about 200:1 to about 300:1, about 200:1 to about 350:1, or about 200:1 to about 400:1. In certain embodiments, the lipid:antigen weight ratio is within a range of about 250:1 to about 300:1, about 250:1 to about 350:1, or about 250:1 to about 400:1. In certain embodiments, the lipid:antigen weight ratio is within a range of about 300:1 to about 350:1, or about 300:1 to about 400:1. In certain embodiments, the lipid:antigen weight ratio is within a range of about 350:1 to about 400:1. In certain embodiments, the lipid:antigen weight ratio is about 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1 or 400:1.

Methods for Making Lipid Vesicles

Several techniques are known for preparing lipid vesicles comprising non-ionic surfactants, such as those referred to in PCT Publication No. WO93/19781. An exemplary technique is the rotary film evaporation method, in which a film of the non-ionic surfactant (and any other component lipids) is prepared by rotary evaporation from an organic solvent, e.g., a hydrocarbon or chlorinated hydrocarbon solvent such as chloroform, e.g., see Russell and Alexander, *J. Immunol.* 140:1274, 1988. The resulting thin film is then rehydrated in aqueous buffer.

Another method for the production of lipid vesicles is that disclosed by Collins et al., *J. Pharm. Pharmacol.* 42:53, 1990. This method involves melting the non-ionic surfactant (and any other component lipids) and hydrating with vigorous mixing in the presence of aqueous buffer.

Another method involves hydration of lipids in the presence of shearing forces. Apparatuses that can be used to apply such shearing forces are well known (e.g., see PCT Publication No. WO88/06882). Sonication and ultra-sonication are also effective means to form lipid vesicles or to alter their size.

In certain embodiments, at least a portion of hemagglutinin antigen is associated with lipid vesicles (where, as used herein, the term "association" encompasses any form of physical interaction). In certain embodiments, at least a portion of hemagglutinin antigen is entrapped within lipid vesicles. Association and entrapment may be achieved in any manner. For example, in the rotary film evaporation technique, the film can be hydrated in the presence of antigen (optionally together with an adjuvant). In other methods, a dehydration-rehydration method may be used in which antigen in an aqueous phase is combined with preformed lipid vesicles and subjected to flash freezing followed by lyophilisation, e.g., see Kirby and Gregoriadis, *Biotechnology* 2:979, 1984. Alternatively or additionally, a freeze thaw technique may be used in which preformed vesicles are mixed with the antigen and repeatedly flash frozen in liquid nitrogen, and warmed to a temperature above the transition temperature of the relevant lipids, e.g., see Pick, *Arch. Biochem. Biophys.* 212:195, 1981. In addition to associating antigen, the dehydration-rehydration method and freeze-thaw technique are also capable of concomitantly associating an adjuvant with lipid vesicles.

In certain embodiments, lipid vesicles for use in accordance with the present invention are prepared by a method that includes: melting component lipids to produce molten lipids; combining the molten lipids with an aqueous solution that includes hemagglutinin antigen; and homogenizing the resulting product. In certain embodiments, molten lipids are added to the aqueous solution that includes hemagglutinin antigen. In certain embodiments, aqueous solution that includes hemagglutinin antigen is added to the molten lipids.

In certain embodiments, molten lipids and aqueous solution are combined in relative amounts and volumes that achieve a lipid concentration of at least about 10 mg/ml in the resulting product. Indeed, through experimentation and as described in the Examples, we have found that when the lipids and antigen are homogenized with a lipid concentration in excess of 10 mg/ml the resulting compositions tend to be more thermostable than when a lower lipid concentration is used (see Examples). In some embodiments, therefore, the present invention provides desirable compositions (specifically including thermostable compositions) comprising antigen and lipid vesicles, which compositions contain a specified lipid concentration established herein to impart particular characteristics (e.g., improved thermostability) to the compositions.

In certain embodiments, a lipid concentration of at least about 15, 20, 25, 30, 35, 40, 45, 50, 55, 60, 65, 70, 75, 80, 85, 90 or 95 mg/ml is achieved. In certain embodiments, the lipid concentration is in a range of about 10 mg/ml to about 15, 20, 25, 30, 35, 40, 45, 50, 55, 60, 65, 70, 75, 80, 85, 90, 95 or 100 mg/ml. In certain embodiments, the lipid concentration is in a range of about 10, 15, 20, 25, 30, 35, 40, 45, 50, 55, 60, 65, 70, 75, 80, 85, 90 or 95 mg/ml to about 100 mg/ml. In certain embodiments, the lipid concentration is in a range of about 25 mg/ml to about 100 mg/ml, about 25 mg/ml to about 75 mg/ml, about 25 mg/ml to about 50 mg/ml, about 50 mg/ml to about 75 mg/ml, or about 50 mg/ml to about 100 mg/ml.

In certain embodiments, molten lipids and aqueous solution are combined in relative amounts and volumes that achieve both the desired lipid:antigen weight ratio (e.g., at least about 50:1 or any one of the aforementioned lipid:antigen weight ratio ranges that were recited above) and a lipid concentration of at least about 10 mg/ml (or any one of the other lipid concentration ranges recited above) in the resulting product.

In certain embodiments, an adjuvant is co-melted with lipids during preparation of provided compositions. In certain embodiments, an adjuvant is combined with molten lipids and aqueous solution that includes influenza virus hemagglutinin antigen during preparation of provided compositions (e.g., by mixing with the aqueous solution that includes influenza virus hemagglutinin antigen before it is combined with molten lipids). In certain embodiments, an adjuvant is added prior to drying (e.g., lyophilization) of provided compositions.

In some embodiments, the non-ionic surfactant (optionally with other lipid components) is melted at a temperature range between 120° C. and 150° C. (e.g., between 120° C. and 125° C., between 120° C. and 130° C., between 120° C. and 140° C., between 130° C. and 140° C., between 135° C. and 145° C., or between 140° C. and 145° C.). In some embodiments, the non-ionic surfactant (optionally with other lipid components) are melted at about 120° C., at about 125° C., at about 130° C., at about 135° C., at about 140° C., at about 145° C. or at about 150° C. In some embodiments, the aqueous solution comprising hemagglutinin antigen is temperature controlled. In some embodiments, the aqueous solution comprising hemagglutinin antigen is kept at a temperature of less than about 50° C. during the step of adding (e.g., less than about 45° C., less than about 40° C., less than about 35° C., less than about 30° C., less than about 25° C., etc.). In some embodiments, the aqueous solution comprising hemagglutinin antigen is kept at a temperature range between about 25° C. and about 50° C. In some embodiments, the aqueous solution comprising hemagglutinin antigen is kept at room temperature.

In certain embodiments, vesicles are made by a process that includes steps of providing the lipid components in dried (e.g., lyophilized) form and rehydrating the dried material with an aqueous solution comprising hemagglutinin antigen. Dried material may be prepared, for example, by melting lipid components and then lyophilizing the molten product.

As described in more detail below, in some embodiments, provided compositions may be dried (e.g., lyophilized) prior to storage and subsequently hydrated prior to use.

Vesicle Size and Processing

Provided compositions will typically include a mixture of lipid vesicles with a range of sizes. In some embodiments >90% of vesicles will have a diameter which lies within 50% of the most frequent value (e.g., 1000±500 nm). In some embodiments the distribution may be narrower, e.g., >90% of vesicles may have a diameter which lies within 40, 30, 20, 10 or 5% of the most frequent value. In some embodiments, sonication or ultra-sonication may be used to facilitate vesicle formation and/or to alter vesicle size. In some embodiments, filtration, dialysis and/or centrifugation may be used to adjust the vesicle size distribution.

In general, lipid vesicles produced in accordance with the present disclosure may be of any size. In certain embodiments, provided compositions may include vesicles where the most frequent diameter is in the range of about 0.1 μm to about 10 μm, for example, about 0.1 μm to about 5 μm, about 0.5 μm to about 2 μm, or about 0.8 μm to about 1.5 μm. In certain embodiments, the most frequent diameter may be greater than 10 μm, e.g., in the range of about 10 μm to about 20 μm or about 15 μm to about 25 μm. In certain embodiments, the most frequent diameter may be in the range of about 0.1 μm to about 20 μm, about 0.1 μm to about 15 μm, about 0.1 μm to about 10 μm, about 0.5 μm to about 20 μm, about 0.5 μm to about 15 μm, about 0.5 μm to about 10 μm, about 1 μm to about 20 μm, about 1 μm to about 15 μm, or about 1 μm to about 10 μm.

Lyophilization

Liquid composition of vaccines has been the default presentation since the introduction of vaccines. Most of the existing liquid vaccines have been developed for storage under refrigeration, but not at higher temperatures, with the result that their stability may not be optimal. All licensed influenza vaccines are currently formulated and stored as liquids. In the aqueous environment the influenza antigens are subjected to physical and chemical degradation that may lead to inactivation and loss of potency.

As discussed above, in certain embodiments, dried (e.g., lyophilized) compositions are provided. In some embodiments, methods of the present disclosure include a step of drying (e.g., lyophilizing).

In general, lyophilization involves freezing the preparation in question and then reducing the surrounding pressure (and optionally heating the preparation) to allow the frozen solvent(s) to sublime directly from the solid phase to gas (i.e., drying phase). The drying phase may be divided into primary and secondary drying phases.

The freezing phase can be done by placing the preparation in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the preparation to a temperature that is below the eutectic point of the preparation. Since the eutectic point occurs at the lowest temperature where the solid and liquid phase of the preparation can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the preparation. The freezing and drying phases are not necessarily distinct phases but can be combined in any manner. For example, in certain embodiments, freezing and drying phases may overlap.

A secondary drying phase can optionally be used to remove residual solvent(s) that was adsorbed during the freezing phase. Once the drying phase is complete, the vacuum can be broken with an inert gas (e.g., nitrogen or helium) before the lyophilized lipid product is optionally sealed.

Excipients such as sucrose, amino acids or proteins such as gelatin or serum albumin may be used to protect the antigen during the drying process and storage. In some embodiments, a lyoprotectant may be used. In some embodiments, adjuvant may be added with the lyoprotectant. Exemplary lyoprotectants include sucrose, trehalose, polyethylene glycol (PEG), dimethyl-succinate buffer (DMS), bovine serum albumin (BSA), mannitol and dextran.

The present disclosure establishes that certain preferred embodiments of provided compositions are those with a particularly low (e.g., less than about 2% by weight) moisture content. Through experimentation (as described in more detail in the Examples), we have determined that dried (e.g., lyophilized) compositions with a higher lipid content tend to have a lower residual moisture content (e.g., less than about 2% by weight). As noted above, compositions with a higher lipid content tend to be more thermostable. Without wishing to be limited to any theory, we hypothesize that some or all of the thermostable properties of the higher lipid content compositions might be driven in part by their lower residual moisture content. Therefore, in certain embodiments, compositions of the present disclosure are defined and provided with low moisture content (e.g., less than about 2% by weight). In certain embodiments, provided compositions have a lipid:antigen weight ratio of at least about 50:1 (or any one of the aforementioned lipid:antigen weight ratio ranges that were recited above). In certain embodiments these compositions may have a lower lipid:antigen weight ratio (e.g., at least about 40:1 or 30:1). Based on our moisture content results, these lower lipid content compositions may require more extensive drying steps during the lyophilization process.

In certain embodiments, the moisture content of provided compositions is less than about 1.9%, 1.8%, 1.7%, 1.6%, 1.5%, 1.4%, 1.3%, 1.2%, 1.1%, 1%, 0.9%, 0.8%, 0.7%, 0.6%, 0.5%, or 0.4% by weight. In certain embodiments, moisture content of provided compositions is in the range of about 0.4% to about 2% by weight. In certain embodiments, moisture content of provided compositions is in the range of about 0.5% to about 1.9% by weight. In certain embodiments, moisture content of provided compositions is in the range of about 0.6% to about 1.8% by weight. In certain embodiments, moisture content of provided compositions is in the range of about 0.7% to about 1.7% by weight. In certain embodiments, moisture content of provided compositions is in the range of about 0.8% to about 1.6% by weight. In certain embodiments, moisture content of provided compositions is in the range of about 0.9% to about 1.5% by weight. In certain embodiments, moisture content of provided compositions is in the range of about 1% to about 1.4% by weight. In certain embodiments, moisture content of provided compositions is in the range of about 0.5% to about 1% by weight. In certain embodiments, moisture content of provided compositions is in the range of about 0.5% to about 1.5% by weight. In certain embodiments, moisture content of provided compositions is in the range of about 0.5% to about 2% by weight. In certain embodiments, moisture content of provided compositions is in the range of about 1% to about 1.5% by weight. In certain embodiments, moisture content of provided compositions is in the range of about 1% to about 2% by weight. In certain embodiments, moisture content of provided compositions is in the range of about 1.5% to about 2% by weight.

Rehydration of Dried Compositions

Dried (e.g., lyophilized) compositions are rehydrated prior to administration to a subject in need thereof. In some embodiments, such rehydration is achieved by mixing the dried (e.g., lyophilized) composition with an aqueous solution. In some embodiments, the aqueous solution includes a buffer. For example, without limitation, a PCB buffer, an $Na_2HPO_4/NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

Storage of Dried Compositions

In certain embodiments, dried (e.g., lyophilized) compositions may be stored for a period of time (e.g., days, weeks or months) prior to rehydration and administration to a subject in need thereof. In certain embodiments, dried (e.g., lyophilized) compositions are stored under conditions that are not temperature-controlled. In certain embodiments, dried (e.g., lyophilized) compositions are at least temporarily exposed to temperatures in excess of 8° C. during storage (e.g., temperatures that exceed 15° C., 20° C. or 25° C.). In certain embodiments, dried (e.g., lyophilized) compositions are at least temporarily exposed to temperatures in the range of 10° C. to 40° C., temperatures in the range of 20° C. to 30° C., room temperature, etc.).

In certain embodiments, dried (e.g., lyophilized) compositions are thermostable. In certain embodiments, dried (e.g., lyophilized) compositions are more stable when stored for 6 months at 40° C. than a reference dried composition that lacks lipid vesicles. In certain embodiments, stability is based on immunogenicity as determined by an HAI assay. In certain embodiments, stability is based on antigen content as determined by an ELISA.

In certain embodiments, dried (e.g., lyophilized) compositions exhibit less than 50% change in immunogenicity as determined by an HAI assay when stored for 6 months at 40° C. In certain embodiments, dried (e.g., lyophilized) compositions exhibit less than 40%, less than 30%, less than 20%, less than 10%, less than 5% or less than 2% change in immunogenicity.

In certain embodiments, dried (e.g., lyophilized) compositions exhibit less than 50% loss of antigen content as determined by an ELISA when stored for 6 months at 40° C. In certain embodiments, dried (e.g., lyophilized) compositions exhibit less than 40%, less than 30%, less than 20%, less than 10%, less than 5% or less than 2% loss of antigen content.

In certain embodiments, these effects are observed after the dried compositions have been stored for just 1, 2 or 3 months instead of 6 months. In certain embodiments, these effects are observed after the dried compositions have been stored at 15° C., 20° C., 25° C., 30° C., or 35° C. instead of 40° C.

In certain embodiments, the antigenicity and/or immunogenicity of dried compositions remains substantially unchanged during storage despite being exposed to temperatures in excess of 8° C. (e.g., temperatures in the range of 10° C. to 40° C., temperatures in the range of 20° C. to 30° C., room temperature, etc.) for a period of 1 to 6 months.

In certain embodiments, storage of dried compositions at these elevated temperatures destroys less than 20% of the antigenicity of the antigen (e.g., less than 15%, less than 10%, less than 5%, less than 1%) as measured in an ELISA and as compared to equivalent dried compositions that were stored between 2 and 8° C. for the same time period.

In certain embodiments, storage of dried compositions at these elevated temperatures destroys less than 20% of the immunogenicity of the antigen (e.g., less than 15%, less than 10%, less than 5%, less than 1%) based on HAI titer measurements and as compared to equivalent dried compositions that were stored between 2 and 8° C. for the same time period.

In certain embodiments, the antigenicity and/or immunogenicity of a dried composition post-storage is at least 1.5 fold greater than in an otherwise equivalent dried composition that was stored under the same elevated temperatures but that was formulated without lipid vesicles (e.g., at least about 2 fold, 2.5 fold, 3 fold, 3.5 fold, 4 fold or 5 fold). In some embodiments, the level of antigenicity is based on measurements obtained using an ELISA. In some embodiments, the level of immunogenicity is based on HAI titer measurements.

In some embodiments, one or more of these antigenicity and/or immunogenicity results are obtained when dried composition is stored at 25° C. for 1, 2, 3 or 4 months. In some embodiments, these results are obtained when the dried composition is stored at 15° C., 20° C., 30° C., 35° C. or 40° C. for 1 month. In some embodiments, these results are obtained when the dried composition is stored at 15° C., 20° C., 30° C., 35° C. or 40° C. for 2 months. In some embodiments, these results are obtained when the dried composition is stored at 15° C., 20° C., 30° C., 35° C. or 40° C. for 3 months. In some embodiments, these results are obtained when the dried composition is stored at 15° C., 20° C., 30° C., 35° C. or 40° C. for 4 months. In some embodiments, these results are obtained when the dried composition is stored at 15° C., 20° C., 30° C., 35° C. or 40° C. for 6 months.

Exemplary Compositions

In certain embodiments, provided compositions do not comprise or are substantially free of additional agents with adjuvant properties (i.e., provided compositions are unadjuvanted). In certain embodiments, provided compositions do not comprise or are substantially free of TLR agonist adjuvants (i.e., TLR-3, TLR-4, TLR-5, TLR-7/8, TLR-9, etc. agonist adjuvants). In certain embodiments, provided compositions do not comprise or are substantially free of TLR-3 agonist adjuvants, e.g., Poly(I:C) or Poly(IC:LC). In certain embodiments, provided compositions do not comprise or are substantially free of TLR-4 agonist adjuvants, e.g., MPL or 3D-MPL. In certain embodiments, provided compositions do not comprise or are substantially free of TLR-5 agonist adjuvants. In certain embodiments, provided compositions do not comprise or are substantially free of TLR-7/8 agonist adjuvants. In certain embodiments, provided compositions do not comprise or are substantially free of TLR-9 agonist adjuvants.

IV. Dosage and Administration

Methods of this disclosure are useful for treating influenza infections in humans including adults and children. In general however they may be used with any animal. In certain embodiments, methods herein are used for veterinary applications, e.g., canine and feline applications. If desired, the methods herein may also be used with farm animals, such as ovine, avian, bovine, porcine and equine breeds.

Compositions described herein will generally be administered in such amounts and for such a time as is necessary or sufficient to induce an immune response. Dosing regimens may consist of a single unit dose or a plurality of unit doses over a period of time. The exact amount of a provided composition to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In certain embodiments, provided compositions include a dose of hemagglutinin antigen in a range from about 1 to 100 μg. For example, in certain embodiments the range may be between about 2 and 50 μg, 5 and 50 μg, 2 and 20 μg, 5 and 20 μg, etc. In certain embodiments, doses of hemagglutinin antigen may be about 5 μg, 10 μg, 15 μg, 20 μg, 25 μg, 30 μg, 35 μg, 40 μg, 45 μg, etc. In certain embodiments these doses are administered as a single unit dose. In certain embodiments a unit dose is administered on several occasions (e.g., 1-3 unit doses that are separated by 1-12 months). In certain embodiments, hemagglutinin antigen is taken from a licensed human influenza vaccine and composition are administered to a human such that the unit dose of hemagglutinin antigen is less than the standard human unit dose (e.g., in the range of 10-90%, 10-80%, 10-70%, 10-60%, 10-50%, 10-40%, 10-30%, 10-20%, 20-90%, 20-80%, 20-70%, 20-60%, 20-50%, 20-40%, 20-30%, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, or 80-90% of the standard human unit dose). For example, if the standard human unit dose calls for a single administration of a composition that includes 45 μg hemagglutinin antigen (e.g., see Fluzone®, Fluvirin® or FluLaval®) then, in certain embodiments, methods of the present disclosure may involve giving the subject a single administration of a provided composition that includes less than 45 μg hemagglutinin antigen, e.g., 40 μg, 35 μg, 30 μg, 25 μg, 20 μg or 15 μg of hemagglutinin antigen.

In some embodiments the amounts of hemagglutinin antigen and TLR-4 agonist adjuvant (e.g., MPL or 3D-MPL) in provided compositions are such that each unit dose includes about 1-100 μg (e.g., about 2-80 μg, 5-70 μg, or about 10-50 μg) hemagglutinin antigen and about 1-100 μg (e.g., about 1-50 μg, about 1.5-50 μg, about 2.5-50 μg, about 2.5-50 μg, about 2.5-40 μg, about 2.5-30 μg, about 2.5-20 μg, or about 2.5-10 μg) TLR-4 agonist adjuvant (e.g., MPL or 3D-MPL).

In certain embodiments, provided compositions are formulated for delivery parenterally, e.g., by injection. In such embodiments, administration may be, for example, intravenous, intramuscular, intradermal, or subcutaneous, or via by infusion or needleless injection techniques. In certain embodiments, compositions may be formulated for intramuscular delivery. For such parenteral administration, compositions may be prepared and maintained in dried form and rehydrated prior to administration as discussed above. The pH of injectable compositions can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Injectable compositions can be sterilized, for example, by filtration through a bacterial-retaining filter, or by incorporating sterilizing agents in the form of sterile solid compositions which can be dissolved or dispersed in sterile water or other sterile injectable medium prior to use.

EXAMPLES

The following examples describe some exemplary modes of making and practicing certain compositions that are described herein. It should be understood that these examples are for illustrative purposes only and are not meant to limit the scope of the compositions and methods described herein.

Example 1

Thermostable Lyophilized Immunogenic Compositions

This Example describes methods for preparing a thermostable lyophilized immunogenic composition for intramuscular (IM) injection. All the non-ionic surfactant vesicle (NISV) compositions were prepared by the inverted melt method. The following lipids were used: 1-monopalmitoyl glycerol (a non-ionic surfactant), cholesterol (a steroid) and dicetyl phosphate (an ionic amphiphile). Specifically, a 5:4:1 molar ratio of lipids (496 mg of 1-monopalmitoyl glycerol (MPG), 464 mg of cholesterol (CHO), and 164 mg of dicetyl phosphate (DCP)) was placed in a flat bottom glass beaker, ensuring none of the powder adhered to the side of the glass beaker. In this exemplary composition phosphorylated hexaacyl disaccharide (ammonium salt) (PHAD, an exemplary TLR-4 agonist adjuvant shown in FIG. 1, available from Avanti Polar Lipids, Inc. of Alabaster, Ala.) was optionally added at either 12 mg (for the dose-sparing compositions) or 4 mg (for the dose-equivalent compositions), and co-melted along with the other lipids. The beaker was clamped and covered with aluminum foil and the lipids were melted in a heated oil bath at 120-125° C. with occasional swirling using a glass rod. While the lipids were melting, a concentrated phosphate buffer was prepared as follows: 5.980 g of $Na_2HPO_4$ and 1.363 g of $NaH_2PO_4$ were dissolved in 20 ml of sterile water, the pH was measured, the solution was filtered through a 0.45 μm sterile filter and 0.796 ml of this buffer was added to 40 ml of Fluzone® influenza vaccine (2009-2010 season; Sanofi Pasteur) in a laminar flow hood. Fluzone® influenza vaccine (2009-2010 season; Sanofi Pasteur) is an inactivated trivalent split influenza vaccine which contains influenza HA antigen at a concentration of 45 μg/0.5 ml (each 0.5 ml contains 15 μg HA antigen from each of the following influenza virus strains: H1N1, A/Brisbane/59/2007; H3N2, A/Brisbane/10/2007 and B/Brisbane/60/2008). The buffered antigen stock solution was homogenized at 8,000 rpm at 30-35° C., and quickly (to prevent crystallization) the melted lipids were transferred into the beaker while homogenizing the solution, at which point homogenization at 8,000 rpm continued for 10 minutes at 30-35° C. The resulting lipid-antigen suspension was shaken for 1-2 hours at 220±10 rpm at 30-35° C. An in-process sample was taken after this step to determine pH and particle size distribution (PSD). Finally, 40 ml of 400 mM sucrose solution in water was added to the 40 ml of NISV-antigen solution and shaken for 5 minutes at 220±10 rpm at 30-35° C. Aliquots were taken (0.5 ml/vial for the dose-sparing compositions and 1.5 ml/vial for the dose-equivalent compositions), frozen at −80° C. overnight or longer and subsequently lyophilized according to the target lyophilization parameters in the lyophilization cycle outlined in Table 2 below and the primary drying time set points given in Table 3 below for different fill volumes.

TABLE 2

| Step | Type | Temperature (° C.) | Time (hours, ±0.3) | Pressure (mTorr) |
|---|---|---|---|---|
| 1* | Hold | Room Temp. | 1.0 | N/A |
| 2 | Ramp | −45 | 1.0 | N/A |
| 3** | Hold | −45 | ≥8.0*** | N/A |
| 4 | Ramp | −30 | 1.0 | N/A |
| 5 | Evacuation | −30 | N/A | 100 |
| 6 | Hold | −30 | See Table 3 | 100 |
| 7 | Ramp | 0 | 1.0 | 100 |
| 8 | Hold | 0 | 3.0 | 100 |
| 9 | Ramp | 20 | 1.0 | 50 |
| 10 | Hold | 20 | 10.0 | 50 |
| 11 | Stopper | Room Temp. | N/A | N/A |

*Sample loading step, if sample is not pre-frozen.

**Sample loading step, if sample is pre-frozen.

***If sample is pre-frozen, the minimum time is 1 hour.

TABLE 3

| Fill Volume (ml) | Time (hours, ±0.3) |
|---|---|
| 0.1-1.0 | 21 |
| 1.1-2.0 | 35 |
| 2.1-3.0 | 43 |
| 3.1-5.0 | 50 |
| 5.1-7.0 | 55 |
| 7.1-10.0 | 60 |

Control samples not formulated with NISVs but containing antigen and adjuvant were prepared according to the following procedure: 12 mg (dose-sparing compositions) or 4 mg (dose-equivalent compositions) of PHAD was resuspended in 40 ml of 400 mM sucrose solution and this suspension was subsequently mixed with 40 ml of Fluzone® influenza vaccine (2009-2010 season; Sanofi Pasteur) and shaken for 5 minutes at 220±10 rpm at 30-35° C. This unformulated antigen-adjuvant solution was aliquoted into vials (0.5 ml/vial for the dose-sparing compositions and 1.5 ml/vial for the dose-equivalent compositions), frozen at −80° C. overnight or longer and subsequently lyophilized according to the target lyophilization parameters in the lyophilization cycle outlined above in Table 2 and the primary drying time set points given above in Table 3 for different fill volumes.

All lyophilized compositions were rehydrated prior to administration in 0.75 ml of WFI. As discussed in more detail below, some of the studies used Fluzone® influenza vaccine as supplied in liquid form as a control (i.e., without any formulation steps including no lyophilization).

Example 2

Influenza Immunization of Mice with Immunogenic Compositions

The compositions prepared as described in Example 1 were tested in female BALB/C mice 6-8 weeks old (minimum 8 animals per test group). The mice were immunized intramuscularly with 50 μl of the control or rehydrated compositions twice, once on day 0 and once on day 14. Blood was collected from all mice in the study groups pre-immunization and then post-$1^{st}$ and -$2^{nd}$ immunizations to assess humoral immune responses. As summarized in Table 4 below, animals received either (1) dose-equivalent Fluzone® (positive control; unformulated and unadjuvanted) at the equivalent of a 0.1× standard human unit dose (a "standard mouse unit dose" is 0.1× of the standard human unit dose, i.e., once the size differences between humans and mice are taken into account) (Group/Test article 1); (2) dose-sparing Fluzone® at the equivalent of a 1/30× standard human unit dose formulated with NISV and the adjuvant PHAD (0.005 mg) (Group/Test article 2); or (3) dose-sparing Fluzone® at the equivalent of a 1/30× standard human unit dose formulated with the adjuvant PHAD (0.005 mg) but no NISVs (Group/Test article 3).

TABLE 4

| Group/Test Article | Fluzone ® (09/10)* | Antigen (μg)**** | Adjuvant (PHAD) (mg)**** | Formulation Type |
|---|---|---|---|---|
| 1*** | 1X human dose (0.1X dose)** | 4.5 | none | none |
| 2 | 1/3X human dose (1/30X dose)** | 1.5 | 0.005 | NISV |

TABLE 4-continued

| Group/Test Article | Fluzone ® (09/10)* | Antigen (μg)**** | Adjuvant (PHAD) (mg)**** | Formulation Type |
|---|---|---|---|---|
| 3 | ⅓X human dose (1/30X dose)** | 1.5 | 0.005 | no NISV |

*Fluzone ® (2009-2010 season; Sanofi Pasteur) is an inactivated trivalent split influenza vaccine. Each 0.5 ml unit dose of Fluzone ® (2009-2010 season; Sanofi Pasteur) contains 15 μg HA antigen from each of the following influenza virus strains: H1N1, A/Brisbane/59/2007; H3N2, A/Brisbane/10/2007; and B/Brisbane/60/2008.
**Mice receive 0.1X of the standard human unit dose of Fluzone ® which correlates approximately to a 1X dose-equivalent or "standard human unit dose" when converting from humans to mice.
***Commercial Fluzone ® control used without any formulation steps.
****Content per 0.05 ml mouse unit dose.

Example 3

Hemagglutination Inhibition Assay of Potency of Immunogenic Compositions

For potency testing, the HAI assay was used to measure immunological responses in animals. The HAI assay is a serological technique used to detect HA antibody in serum resulting from infection or vaccination with influenza virus. HAI titers correlate with protection from influenza in humans. The HAI antibody titer is expressed as the reciprocal of the highest serum dilution showing complete hemmaglutination using four hemagglutination units. An HAI titer of 1:40 or higher is considered as seroprotective, and a four-fold increase in HAI titers in samples taken after and before vaccination is the minimum increase considered necessary for classification of seroconversion. Results are presented as the inverse of HAI titers and geometric mean HAI titers. The HAI assay was performed as follows. Briefly, a series of 2-fold dilutions in PBS of sera from immunized mice were prepared in 96-well V-bottomed plates and incubated at room temperature for 30 minutes with 50 μl of four hemagglutinating units (HAU) of A/Brisbane/59/07 (H1N1) or A/Brisbane/10/2007 (H3N2). Next, 50 μl of chicken red blood cells (diluted 0.5% v/v) (Canadian Food Inspection Agency, Ottawa, Canada) was added to all wells on the plate and incubated for 1.5 hours at room temperature. The highest dilution capable of agglutinating chicken red blood cells was then determined.

Geometric mean, median and standard error of the mean were determined. Statistical analysis was carried out using the Software GraphPad Prism 5. Paired samples were assessed by paired-t test and non-paired samples by student t-test. The p values ≤0.05 were considered to be statistically significant. A positive response was indicated by ≥2-fold increase of 14 day post vaccination responses after the last immunization as compared to the values obtained before immunization. The results of these assays are described below.

In this mouse study we evaluated the potency of the three compositions described in Example 2, Table 4. HAI assays were performed on bleedings obtained from mice on study day 13 (P1Vd13) and day 29 (P2Vd15).

Figure 3:
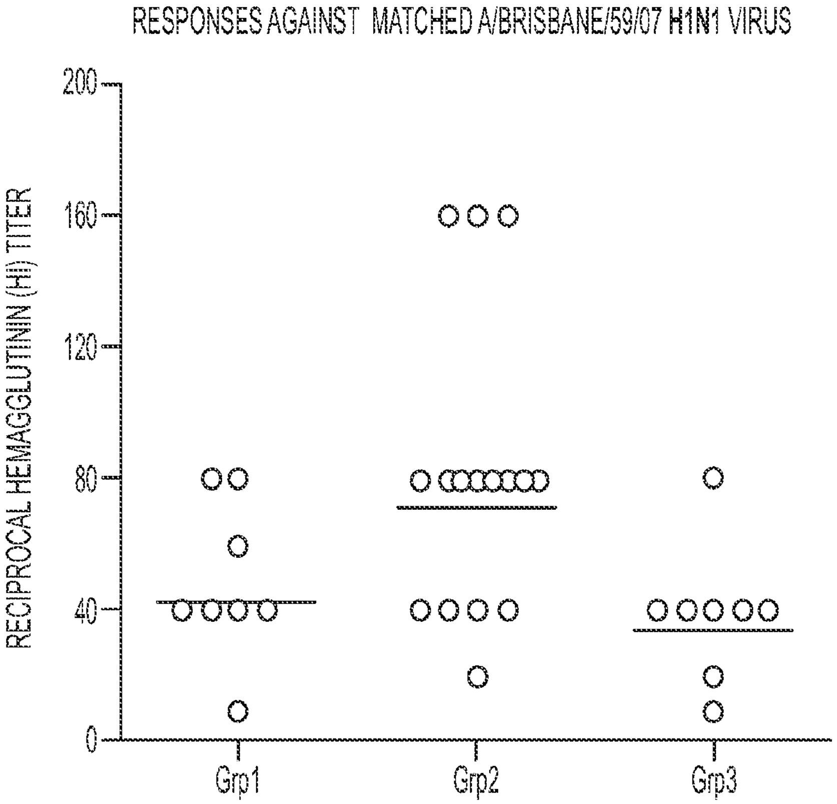
FIG. 3 shows the potency against H1N1 virus of an exemplary licensed influenza vaccine in mice (dose-sparing at 1/30 standard human unit dose where a "standard mouse unit dose" is 0.1× of the standard human unit dose, i.e., once the size differences between humans and mice are taken into account) either formulated with NISV (Group 2) or not formulated with NISV (Group 3) with the exemplary TLR-4 agonist adjuvant PHAD compared to the licensed influenza vaccine (dose-equivalent at 0.1× standard human unit dose where a "standard mouse unit dose" is 0.1× of the standard human unit dose, i.e., once the size differences between humans and mice are taken into account) without formulation into NISV or adjuvant (Group 1) as described in Example 2, Table 4.

FIG. 3 shows the mean HAI titer against H1N1 A/Brisbane/59/07 thirteen days after the first immunization (P1Vd13). It can be seen that the mean HAI titer against H1N1 for Group 2 animals (Table 4; adjuvanted dose-sparing NISV Fluzone® composition) was significantly higher than Group 3 animals (Table 4; adjuvanted dose-sparing Fluzone® composition without NISVs) and also higher than control Group 1 animals (Table 4; unadjuvanted and unformulated dose-equivalent Fluzone®). It was also observed that the adjuvanted dose-sparing NISV Fluzone® composition (Group 2) had higher potency than the control unadjuvanted and unformulated dose-equivalent Fluzone® (Group 1) at one third of the unit dose while the adjuvanted dose-sparing Fluzone® composition without NISVs (Group 3) did not.

Figure 4:
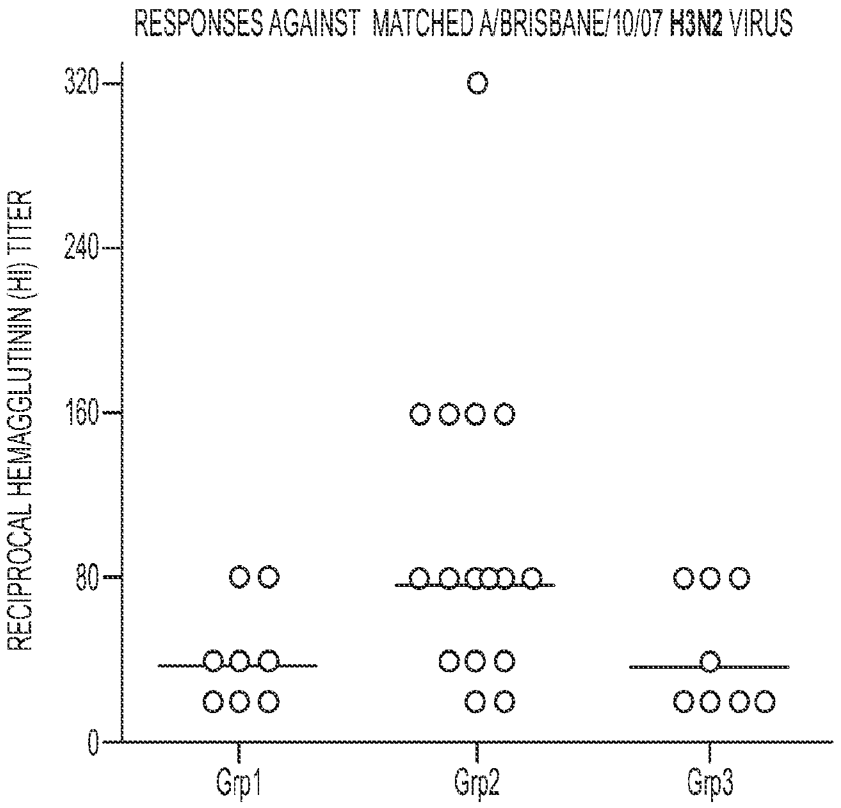
FIG. 4 shows the potency against H3N2 virus of an exemplary licensed influenza vaccine in mice (dose-sparing at 1/30 standard human unit dose) either formulated with NISV (Group 2) or not formulated with NISV (Group 3) with the exemplary TLR-4 agonist adjuvant PHAD compared to the licensed influenza vaccine (dose-equivalent at 0.1× standard human unit dose) without formulation into NISV or adjuvant (Group 1) as described in Example 2, Table 4.

FIG. 4 shows the mean HAI titer against H3N2 A/Brisbane/10/07 thirteen days after the first immunization (P1Vd13). It can be seen that the mean HAI titer against H3N2 for Group 2 animals (Table 4; adjuvanted dose-sparing NISV Fluzone® composition) was significantly higher than Group 3 animals (Table 4; adjuvanted dose-sparing Fluzone® composition without NISVs) and also higher than control Group 1 animals (Table 4; unadjuvanted and unformulated dose-equivalent Fluzone®). Again, it was also observed that the adjuvanted dose-sparing NISV Fluzone® composition (Group 2) had higher potency than the control unadjuvanted and unformulated dose-equivalent Fluzone® (Group 1) at one third of the unit dose while the adjuvanted dose-sparing Fluzone® composition without NISVs (Group 3) did not. Similar trends were observed in the immune responses of animals in the various groups after the second immunization (P2Vd15). In general, HAI titers measured fifteen days after the second immunization (P2Vd15) were approximately 4-5 fold higher than HAI titers observed thirteen days after the first immunization.

To determine the dose dependency of the exemplary TLR-4 agonist adjuvant PHAD on immune response, a positive control and 5 different NISV compositions prepared by the method described in Example 1 (except with increasing amounts of PHAD co-melted with the other lipids) were tested in female BALB/C mice 6-8 weeks old (minimum 8 animals per test group). The six test groups are summarized below in Table 5. The mice were immunized intramuscularly with 50 μl of the control or rehydrated compositions twice, once on day 0 and once on day 14. Serum samples were collected from all mice in the study groups pre-immunization and then post-1$^{st}$ and -2$^{nd}$ immunizations and analyzed using an HAI assay as described in Example 3.

TABLE 5

| Group/Test Article | Fluzone ® (09/10)* | Adjuvant (PHAD) (mg)**** | Formulation Type |
|---|---|---|---|
| 1*** | 1X human dose (0.1X dose)** | none | none |
| 2 | ⅓X human dose (1/30X dose)** | none | NISV |
| 6 | ⅓X human dose (1/30X dose)** | 0.001 | NISV |
| 5 | ⅓X human dose (1/30X dose)** | 0.005 | NISV |
| 4 | ⅓X human dose (1/30X dose)** | 0.015 | NISV |
| 3 | ⅓X human dose (1/30X dose)** | 0.050 | NISV |

*Fluzone ® (2009-2010 season; Sanofi Pasteur) is an inactivated trivalent split influenza vaccine. Each 0.5 ml unit dose of Fluzone ® (2009-2010 season; Sanofi Pasteur) contains 15 μg HA antigen from each of the following influenza virus strains: H1N1, A/Brisbane/59/2007; H3N2, A/Brisbane/10/2007; and B/Brisbane/60/2008.
**Mice receive 0.1X of the standard human unit dose of Fluzone ® which correlates approximately to a 1X dose-equivalent or "standard human unit dose" when converting from humans to mice.
***Commercial Fluzone ® control used without any formulation steps.
****Content per 0.05 ml mouse unit dose.

Figure 5A:
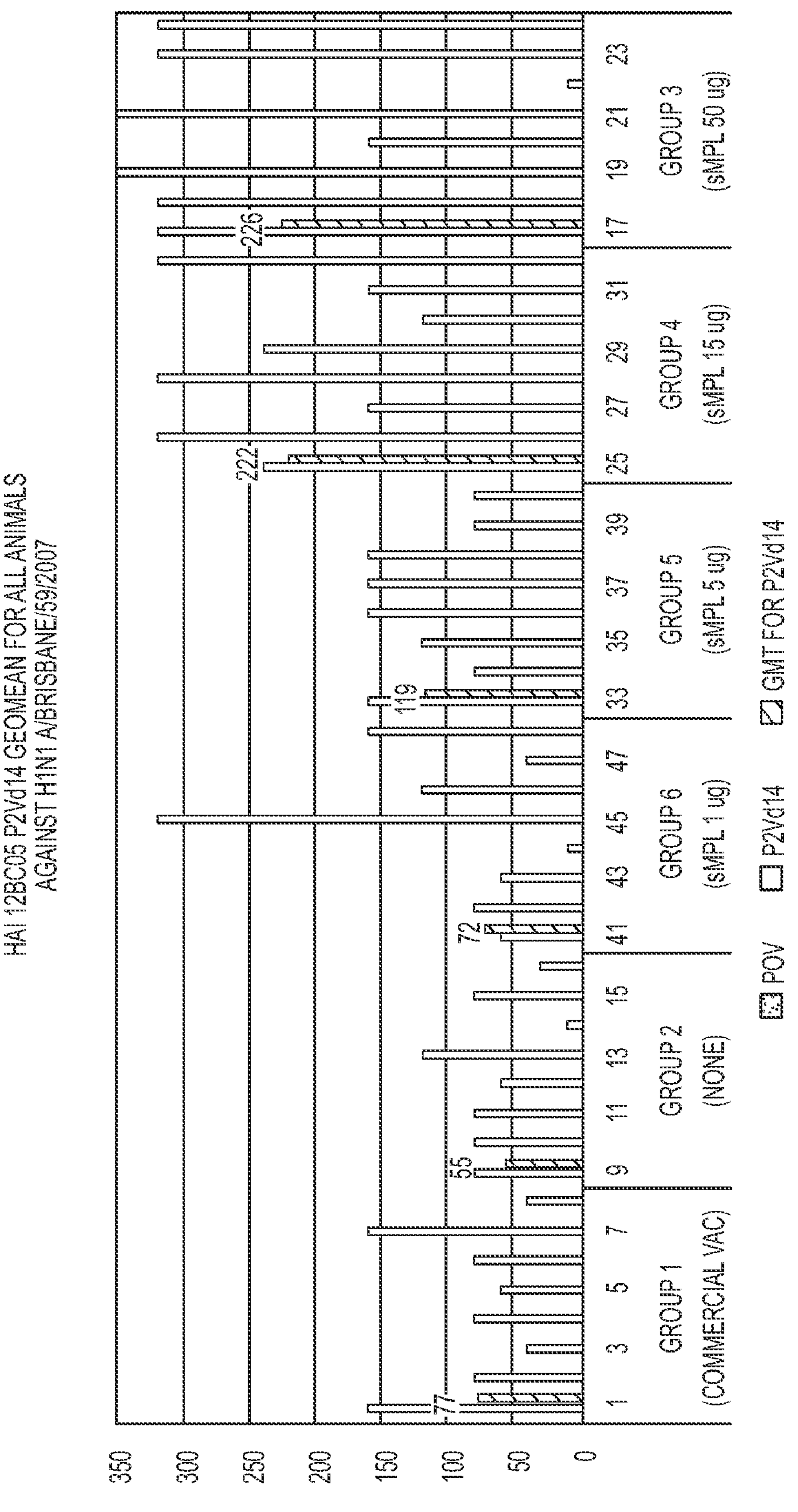
FIG. 5 shows the potency dose response against H1N1 virus (A) and H3N2 virus (B) of an unformulated (i.e., used "as is") licensed influenza vaccine in mice (dose-equivalent at 0.1× standard human unit dose) versus the licensed influenza vaccine formulated with NISV (dose-sparing at 1/30× standard human unit dose) and unadjuvanted or formulated with NISV with increasing amounts (1-50 μg) of the exemplary TLR-4 agonist adjuvant PHAD. All compositions were injected into mice IM and sera were tested 15 days after the second immunization. The results are presented as HAI titers against H1N1 and H3N2 and the geometric mean(s) for the same data set(s).
Figure 5B:
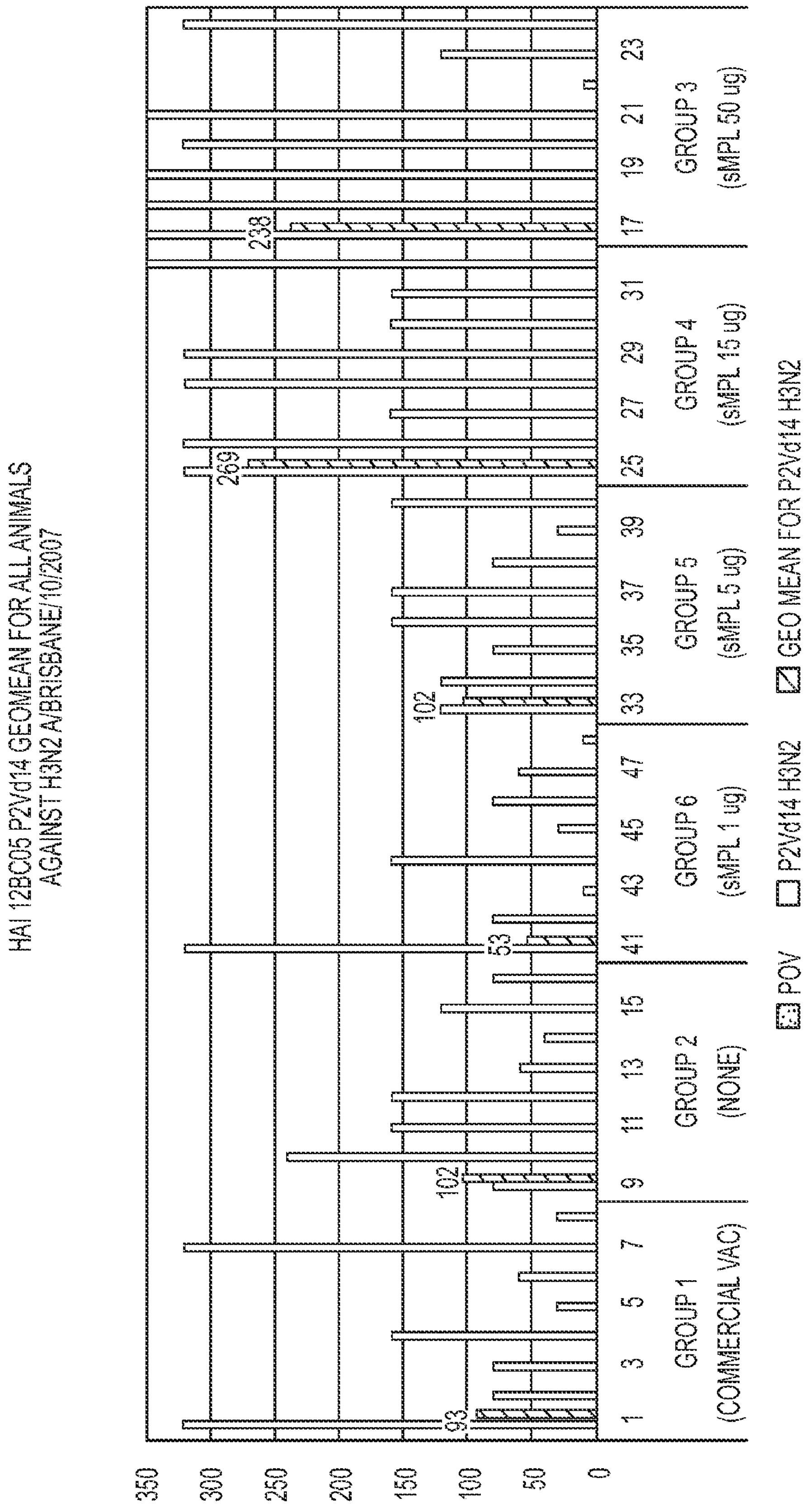

FIG. 5 shows the potency dose response in mice as determined by the HAI titer assay of Example 3 using sera samples taken 15 days post 2$^{nd}$ vaccination. As can be seen in FIG. 5, 5 μg of PHAD (Group 5) increased the potency of the dose-sparing NISV Fluzone® composition to approximately match the potency of the control unadjuvanted and unformulated dose-equivalent Fluzone® (Group 1) whereas the higher doses of PHAD (15 and 50 μg) (Groups 4 and 3, respectively) increased the potency to approximately three times that of the control. FIGS. 5A and B show that the exemplary TLR-4 agonist adjuvant PHAD adjuvant increased potency in a dose-dependent manner for both H1N1 and H3N2.

Example 4

Thermostability Testing of Lyophilized Immunogenic Compositions

The stability of lyophilized immunogenic compositions (NISVs) prepared in accordance with Example 1 was evaluated at three storage temperature conditions (5° C.±3° C., 25° C.±2° C. and 40° C.±2° C.) for up to 6 months. There is no single stability-indicating assay or parameter that profiles the stability characteristics of a biological product. As defined by the FDA (FDA Guidance for Industry. Content and Format of Chemistry, Manufacturing and Controls Information and Establishment Description Information for a Vaccine or Related Product), a stability study for a biological product should generally test for: potency; physicochemical measurements that are stability indicating; moisture content (if lyophilized); pH; sterility or control of bioburden; pyrogenicity and general safety. Consequently, a stability-indicating profile using a number of assays provides assurance that changes in the identity, purity and potency of the biological product is typically detected.

As used herein, the term "potency" refers to the specific ability or capacity of a product to achieve its intended effect and is determined by a suitable in vivo or in vitro quantitative method. An in vivo mouse potency assay was used to evaluate the potency of the stored compositions over time and at the three different storage temperatures. As shown in Table 6 below, control and lyophilized compositions were stored at different temperatures for up to 6 months, after which time they were rehydrated (in the case of lyophilized compositions) and administered IM to mice (as described in Example 2) Immune responses were then determined using the HAI assay of Example 3.

TABLE 6

| Group/Test Article | Fluzone ® (09/10)* | Antigen (μg)**** | Lipid:Antigen ratio# | Adjuvant (PHAD) (mg)**** | Formulation Type |
|---|---|---|---|---|---|
| 1*** | 1X human dose (0.1X dose)** | 4.5 | N/A | none | none |
| 2 | ⅓X human dose (1/30X dose)** | 1.5 | 312:1 | 0.005 | NISV |
| 3 | ⅓X human dose (1/30X dose)** | 1.5 | N/A | 0.005 | no NISV |
| 4 | ⅓X human dose (1/30X dose)** | 1.5 | 312:1 | none | NISV |
| 5 | 1X human dose (0.1X dose)** | 4.5 | 312:1 | 0.005 | NISV |
| 6 | 1X human dose (0.1X dose)** | 4.5 | N/A | 0.005 | no NISV |
| 7 | 1X human dose (0.1X dose)** | 4.5 | 312:1 | none | NISV |

*Fluzone ® (2009-2010 season; Sanofi Pasteur) is an inactivated trivalent split influenza vaccine. Each 0.5 ml unit dose of Fluzone ® (2009-2010 season; Sanofi Pasteur) contains 15 μg HA antigen from each of the following influenza virus strains: H1N1, A/Brisbane/59/2007; H3N2, A/Brisbane/10/2007; and B/Brisbane/60/2008.

**Mice receive 0.1X of the standard human unit dose of Fluzone ® which correlates approximately to a 1X dose-equivalent or "standard human unit dose" when converting from humans to mice.

***Commercial Fluzone ® control used without any formulation steps.

****Content per 0.05 ml mouse unit dose.

#Vesicle forming lipids:HA antigen weight ratio.

The compositions were also analyzed for appearance (color and opacity) and following rehydration were analyzed for particle size distribution (PSD) and pH. Aliquots of rehydrated samples were centrifuged in an ultracentrifuge at 24,000 rpm, for 20 minutes at 4° C. and supernatant and pellet fractions were removed, extracted and analyzed by sELISA to determine antigen content (also described as "in vitro potency"). The stability of rehydrated material was tested over 4-6 hours following rehydration. At the specified time points, the lipids in the lyophilized compositions were analyzed for purity and degradants using HPLC. Moisture content in the lyophilized compositions was evaluated using the Karl Fischer assay. The compositions used for the stability study were not sterile. However, the formulation method involved heating the lipids to >100° C. and adding the molten lipids to a sterile filtered buffer solution containing sterile Fluzone®. The formulation methods were performed under low microbial content (bioburden) conditions such as in a lamellar flow hood and using Tyvek sterile bags during lyophilization and back filled using sterile nitrogen. Bioburden was evaluated as Total Aerobic Microbial Count (CFU per gram) by plating samples on Tryptic Soy Agar (TSA) and incubating for 3-5 days at 30-35° C. and as Total Combined Yeasts and Molds Count (CFU per gram) by plating samples on Sabouraud Agar (SDA) and incubating for 5-7 days at 20-25° C.

The general recommendations, as outlined in the ICH Harmonized Tripartite Guideline: Stability Testing of New Drug Substances and Products. Q1A(R2), were followed during the execution of the stability study. The proposed stability indicating tests are listed in Table 7 below where a "month" was approximately 4 weeks and X indicates a required test while O indicates an optional test.

TABLE 7

| | Time points (month) and animal experiments | | | |
|---|---|---|---|---|
| Test/Assay | T = 0 | T = 1 | T = 3 | T = 6 |
| Potency (in vivo mouse) | X | X | X | X |
| ELISA (in vitro potency) | X | X | X | X |
| Appearance | X | X | X | X |
| Moisture | X | X | X | X |
| Bioburden | X | X | X | X |
| SRID | O | O | O | O |
| PSD | X | X | X | X |
| pH | X | X | X | X |
| HPLC | O | O | O | O |

FIG. 6 shows the in vivo potency in mice (HAI titers assayed as described in Example 3 using sera samples taken 15 days post 2$^{nd}$ vaccination) of a dose-sparing adjuvanted NISV Fluzone® composition (Group 2: NISV, TLR-4 agonist adjuvant) versus a dose-sparing adjuvanted Fluzone® composition (Group 3: no NISV, TLR-4 agonist adjuvant) and a dose-equivalent unadjuvanted and unformulated Fluzone® control (Group 1: no NISV, no TLR-4 agonist adjuvant). The control and lyophilized compositions were stored for 6 months at 4° C. or 40° C. prior to IM injection into mice as described in Example 2. As can be seen in FIG. 6, the HAI titers for H1N1 and H3N2 demonstrate that the dose-sparing adjuvanted NISV Fluzone® composition (Group 2) was equally potent when stored for up to 6 months at 4° C. or 40° C., whereas the dose-equivalent unadjuvanted and unformulated Fluzone® control (Group 1) and dose-sparing adjuvanted Fluzone® composition (Group 3) both lost potency when stored at 40° C. versus 4° C. over the same 6 month time period.

Figure 7:
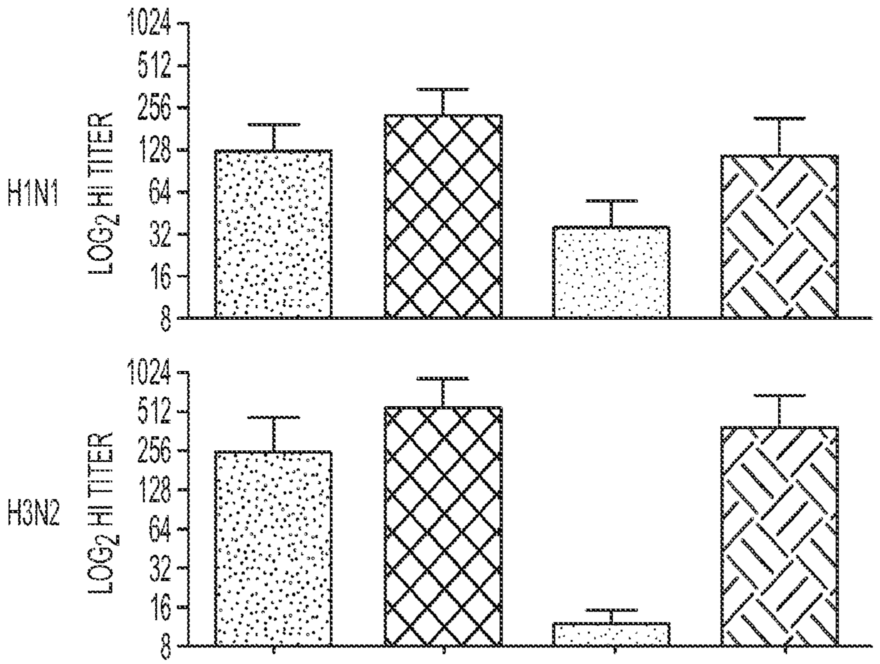
FIG. 7 shows the potency against H1N1 virus and H3N2 virus of an unadjuvanted exemplary licensed influenza vaccine in mice (dose-equivalent at 0.1× standard human unit dose) formulated with NISV compared to the licensed influenza vaccine (dose-equivalent at 0.1× standard human unit dose) as described in Example 4, Table 6. All compositions were stored at 4° C. and 40° C. for 6 months and then injected into mice IM and sera were tested 15 days after the second immunization. The results are presented as HAI titers against H1N1 or H3N2.

FIG. 7 shows the in vivo potency in mice (HAI titers assayed as described in Example 3 using sera samples taken 15 days post 2$^{nd}$ vaccination) for a dose-equivalent unadjuvanted NISV Fluzone® composition (Group 7: NISV, no TLR-4 agonist adjuvant) versus the dose-equivalent unadjuvanted and unformulated Fluzone® control (Group 1: no NISV, no TLR-4 agonist adjuvant). The control and lyophilized compositions were stored for 6 months at 4° C. or 40° C. prior to IM injection into mice as described in Example 2. As can be seen in FIG. 7, the HAI titers for H1N1 and H3N2 demonstrate that the dose-equivalent unadjuvanted NISV Fluzone® composition (Group 7) was equally potent when stored for up to 6 months at 4° C. or 40° C., whereas the dose-equivalent unadjuvanted and unformulated Fluzone® control (Group 1) lost potency when stored at 40° C. versus 4° C. over the same 6 month time period.

Figure 8B:
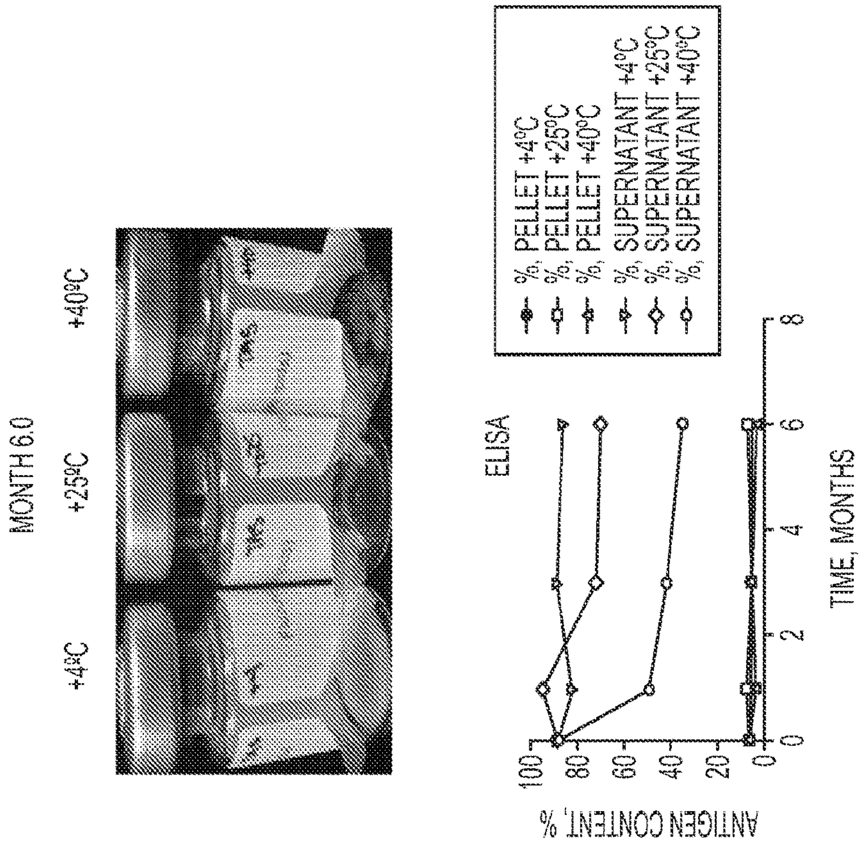
FIG. 8 shows in vitro data of HA antigen content for commercial Fluzone® that was: (A) formulated with NISVs or (B) without NISVs as determined by sELISA; T=0, 1, 3 and 6 months stored at 4° C., 25° C. and 40° C. Both compositions were dose-sparing and adjuvanted with the exemplary TLR-4 agonist adjuvant PHAD.
Figure 8A:
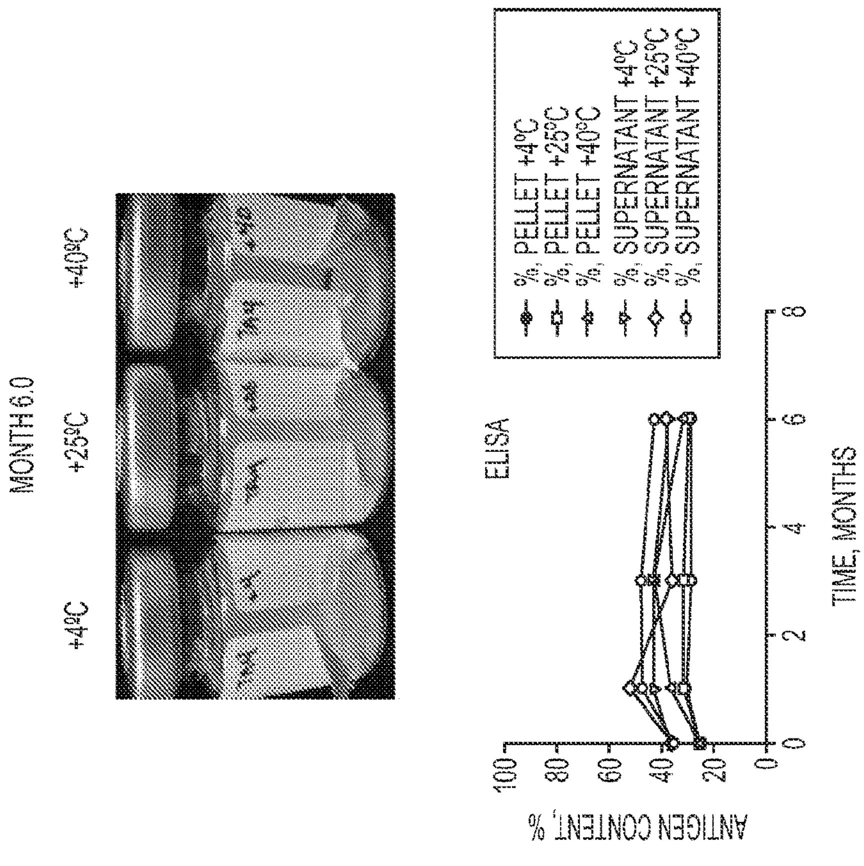

FIG. 8 shows in vitro HA antigen content after different storage periods (timepoints T=0, 1, 3, and 6 months) and temperatures (4° C., 25° C. and 40° C.) for the following compositions: (A) dose-sparing adjuvanted NISV Fluzone® composition (Group 2) and (B) dose-sparing adjuvanted Fluzone® composition (Group 3). The HA antigen content values were determined by sELISA as described above. Compositions were centrifuged and the amounts of HA antigen in the pellet and supernatant were measured separately as shown. As can be seen in FIG. 8, the results demonstrate minimal loss of HA antigen content when Fluzone® was formulated with NISVs and stored up to 6 months at 40° C. (Group 2, FIG. 8A), whereas HA content declined steadily when Fluzone® was not formulated with NISVs and stored at 40° C. (Group 3, FIG. 8B).

Appearance:

The most noticeable time and temperature-dependent change in appearance was the melting of the lyophilized cakes which was observed in all of the lyophilized non-NISVs containing control compositions after storage at 40° C. and to a lesser extent at 25° C. Without wishing to be bound by any theory, the melting of the lyophilized cakes observed in these non-NISV lyophilized compositions did not appear to be due to incomplete drying of cakes prior to the start of secondary drying. The lyophilized cakes were all satisfactory following lyophilization but shrank and liquefied at increasingly elevated temperatures over storage time.

Residual Moisture:

The residual moisture in lyophilized cakes was determined using the Karl Fischer assay and was expressed as percent moisture by weight. Without wishing to be bound by any theory, it appeared that residual moisture content of the lyophilized cake may inversely correlate with stability of the composition. It was observed that, at time zero (directly after lyophilization), the total residual moisture in the lyophilized non NISV-containing composition groups was higher than the residual moisture in the lyophilized NISV-containing compositions: about 2-4% versus about 1-2% residual moisture, respectively. In general, the presence of NISVs during lyophilization resulted in lower residual moisture content.

There were very minimal to no observable changes in the residual moisture of the lyophilized NISV-containing compositions when stored at elevated temperatures (e.g., 25° C., 40° C.) for extended periods of time (e.g., up to 6 months) (data not shown).

Particle Size Distribution:

There were apparent changes in the size distribution and the mean particle size at 40° C. (and to a much lesser extent at 25° C.) in both lyophilized NISV-containing and non NISV-containing compositions (data not shown). These changes in the particle size distribution and the mean particle size were not observed at 4° C. for any NISV-containing compositions.

pH: The pH of all the compositions was approximately the same when stored at 4° C., 25° C. or 40° C. and showed no observable trend over the course of the six month study.

Example 5

Thermostability of Lyophilized Immunogenic Compositions with Other Adjuvants and Antigens The objective of this study was to determine if different types of adjuvants and antigens would be thermostable when formulated with NISVs. Note that no optimization of the various composition(s) was completed in order to test these alternative adjuvants and antigens (e.g., optimization of adjuvant concentration, etc.).

Different Adjuvants:

All the non-ionic surfactant vesicle (NISV) compositions with different adjuvants were prepared by the inverted melt method as described in Example 1. Specifically, for each composition a 5:4:1 molar ratio of lipids (147.59 mg MPG, 138.25 mg CHO and 49.66 mg DCP) was placed in a flat bottom glass beaker. The beaker was clamped and covered and the lipids were melted in a heated oil bath at 120° C.-125° C. with occasional swirling using a glass rod. Concentrated phosphate buffer, prepared as described in Example 1 (0.224 ml) was added to 11.67 ml of Fluzone® influenza vaccine (2010-2011 season; Sanofi Pasteur) in a laminar flow hood. The buffered antigen stock solutions were homogenized at 8000 rpm at 30-35° C., and quickly (to prevent crystallization) the melted lipids were transferred into the beaker while homogenizing the solution. Homogenization at 8000 rpm continued for 10 minutes at 30-35° C. The resulting lipid-antigen suspension was shaken for 1-2 hours at 220±10 rpm at 30° C.-35° C. An equivalent volume of 400 mM sucrose solution in water was added with each adjuvant (3.5 mg adjuvant) to each of the NISV-antigen solutions and shaken for 5 minutes at 220±10 rpm at 30° C.-35° C. Aliquots were taken (0.5 ml/vial), frozen at −80° C. overnight or longer and subsequently lyophilized according to the target lyophilization parameters in the lyophilization cycle outlined in Table 2 and the primary drying time set points given in Table 3 for different fill volumes.

Lyophilized adjuvanted compositions were stored for 3 months at 4° C. or 40° C. and then rehydrated in 0.75 ml of WFI prior to IM injection into mice as described in Example 2. The in vivo potency of the rehydrated compositions was assayed (HAI titers against H1N1 were measured as described in Example 3) in sera samples taken from vaccinated mice 15 days post 2$^{nd}$ vaccination. The results are shown below in Table 8. These results demonstrate that the dose-sparing adjuvanted Fluzone® compositions (Groups 1 and 2) are equally potent when stored for up to 3 months at 4° C. or 40° C. irrespective of adjuvant type. The overall potency of these dose-sparing adjuvanted NISV Fluzone® compositions (Groups 1 and 2) was less than the overall potency of a dose-equivalent NISV Fluzone® composition (Group 3). A study was also performed with flagellin (a TLR-5 agonist adjuvant); however, the dose tested was toxic to the mice.

TABLE 8

| Group/ Test Article | Fluzone ® (10/11) Content (μg)* | Adjuvant Type | Adjuvant Content (μg) | Formulation Type | HAI GMT H1N1 P2Vd14 T = 3 months at 4° C. | HAI GMT H1N1 P2Vd14 T = 3 months at 40° C. |
|---|---|---|---|---|---|---|
| 1 | 1.5 | CL097** | 5 | NISV | 177 | 121 |
| 2 | 1.5 | CpG*** | 5 | NISV | 184 | 211 |
| 3 | 4.5 | N/A | N/A | NISV | 421 | 354 |

*Fluzone ® (2010-2011 season; Sanofi Pasteur) is an inactivated trivalent split influenza vaccine. Each 0.5 ml unit dose of Fluzone ® (2010-2011 season; Sanofi Pasteur) contains 15 μg HA antigen from each of the following influenza virus strains: H1N1, A/California/07/2009 X-179A. H3N2, A/Victoria/210/2009 X-187; and B/Brisbane/60/2008.

**TLR 7/8 agonist adjuvant.

***TLR 9 agonist adjuvant.

Different Antigens:

Non-ionic surfactant vesicles (NISV) compositions of different influenza antigens were prepared by the inverted melt method as described in Example 1. Specifically, for each composition a 5:4:1 molar ratio of lipids (404 mg MPG, 378 mg CHO and 134 mg DCP) was placed in a flat bottom glass beaker. The beaker was clamped and covered and the lipids were melted in a heated oil bath at 120° C.-125° C. with occasional swirling using a glass rod. Concentrated phosphate buffer, prepared as described in Example 1 (0.615 ml) was added to 32 ml of Fluzone® influenza vaccine (2010-2011 season; Sanofi Pasteur), Fluvirin® influenza vaccine (2010-2011 season; Novartis), or FluLaval® influenza vaccine (2010-2011 season; GSK) in a laminar flow hood. Fluzone® influenza vaccine (2010-2011 season; Sanofi Pasteur) is an inactivated trivalent split influenza vaccine which contains influenza HA antigen at a concentration of 45 μg/0.5 ml (each 0.5 ml contains 15 μg HA antigen from each of the following influenza virus strains: H1N1, A/California/07/2009 X-179A. H3N2, A/Victoria/210/2009 X-187; and B/Brisbane/60/2008). Fluvirin® influenza vaccine (2010-2011 season; Novartis) is an inactivated trivalent split influenza vaccine which contains influenza HA antigen at a concentration of 45 μg/0.5 ml (each 0.5 ml contains 15 μg HA antigen from each of the following influenza virus strains: H1N1, A/California/07/2009 X-181; H3N2, A/Victoria/210/2009 X-187; and B/Brisbane/60/2008). FluLaval® influenza vaccine (2010-2011 season; GSK) is also an inactivated trivalent split influenza vaccine which contains influenza HA antigen at a concentration of 45 μg/0.5 ml (each 0.5 ml contains 15 μg HA antigen from each of the following influenza virus strains: H1N1, A/California/07/2009 X-181; H3N2, A/Victoria/210/2009 X-187; and B/Brisbane/60/2008). The buffered antigen stock solutions were homogenized at 8000 rpm at 30-35° C., and quickly (to prevent crystallization) the melted lipids were transferred into the beaker while homogenizing the solution, at which point homogenization at 8000 rpm continued for 10 minutes at 30-35° C. The resulting lipid-antigen suspension was shaken for 1-2 hours at 220±10 rpm at 30° C.-35° C. An equivalent volume of 400 mM sucrose solution in water was added to each of the NISV/ antigen solutions and shaken for 5 minutes at 220±10 rpm at 30° C.-35° C. Aliquots were taken (1.5 ml/vial), frozen at −80° C. overnight or longer and subsequently lyophilized according to the target lyophilization parameters in the lyophilization cycle outlined in Table 2 and the primary drying time set points given in Table 3 for different fill volumes.

Figure 9:
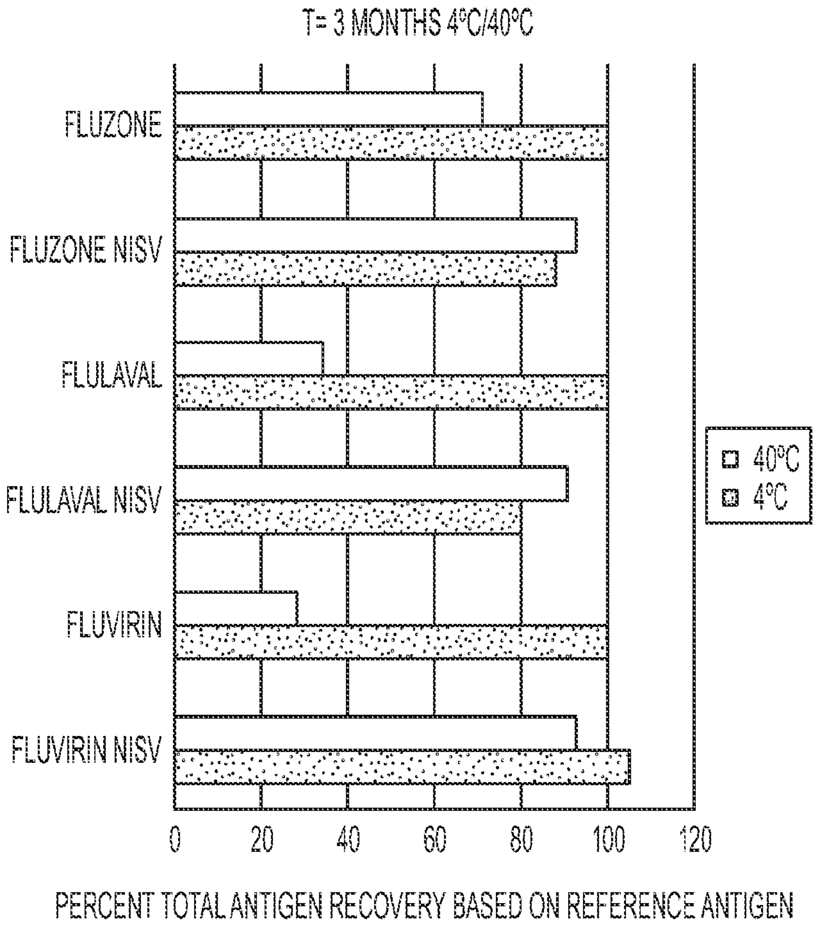
FIG. 9 shows in vitro data of HA antigen content for unformulated commercial influenza vaccines Fluzone®, Fluvirin® and FluLaval® versus the same commercial influenza vaccines formulated with NISVs. Aliquots of reconstituted samples were analysed by sELISA to determine antigen content (or "in vitro potency") for the compositions at T=3 months at 4° C. and 40° C.

The compositions were stored for 3 months at 4° C. and 40° C. and then rehydrated in 0.75 ml of WFI prior to IM injection into mice as described in Example 2. FIG. 9 shows the "in vitro potency" of the compositions after 3 months at 4° C. or 40° C. (HA antigen content determined by sELISA, as described in Example 4). The results demonstrate minimal loss of HA antigen content with storage up to 3 months at 40° C. when the influenza antigens (Fluzone®, Fluvirin® or FluLaval®) were formulated with NISVs, whereas HA antigen content declined steadily when the influenza antigens (Fluzone®, Fluvirin® or FluLaval®) were not formulated with NISVs.

Example 6

Influenza Immunization of Monkeys with Immunogenic Compositions

Figure 10:
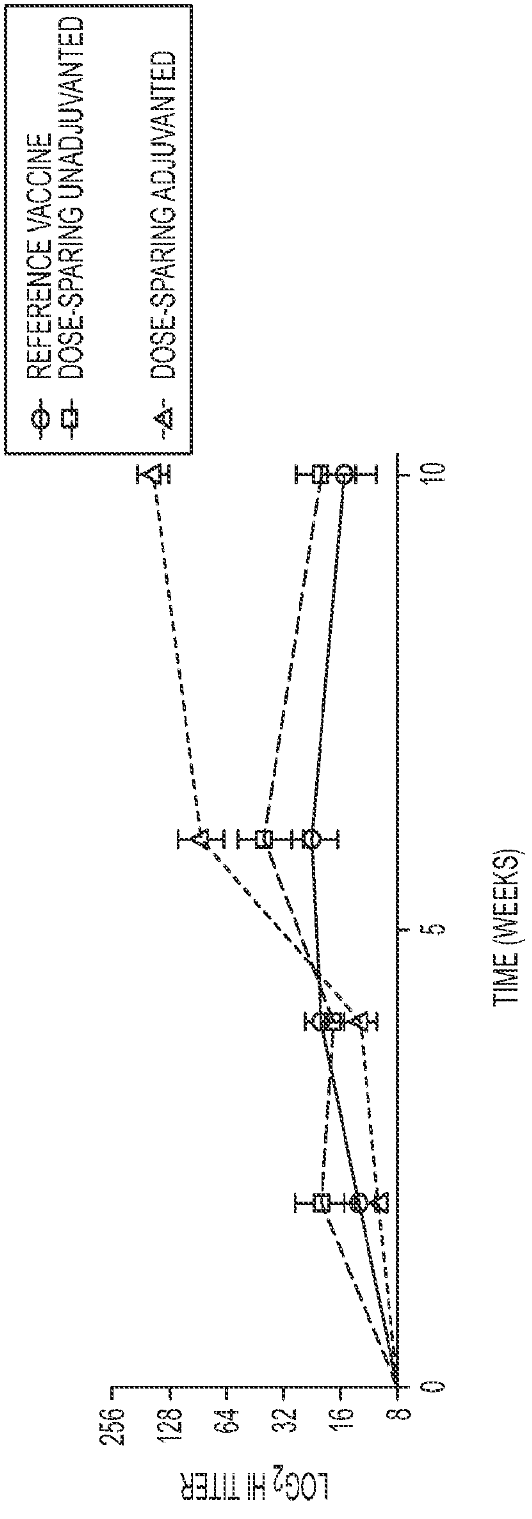
FIG. 10 shows the potency against H3N2 virus of an exemplary licensed influenza vaccine (dose-sparing at 1/3× standard human unit dose, where a "standard monkey unit dose" is 1× of the standard human unit dose) in rhesus macaques either formulated with NISV and adjuvanted with the exemplary TLR-4 agonist adjuvant PHAD or formulated with NISV and unadjuvanted compared to the licensed influenza vaccine (dose-equivalent at 1× standard human unit dose, where a "standard monkey unit dose" is 1× of the standard human unit dose) without formulation into NISV or adjuvant.

To examine immunogenicity in a non-human primate model, the compositions that had demonstrated thermostability in vitro and in vivo in mice at 4° C., 25° C., and 40° C. for up to 6 months were also tested in rhesus macaques. Monkeys received two injections (0, 28 days) of either (a) a dose-equivalent amount (1× standard human unit dose or 45 μg) of unadjuvanted and unformulated Fluzone® positive control or (b) a dose-sparing amount (⅓× standard human unit dose or 15 μg) of Fluzone® formulated with NISVs with or without the exemplary TLR-4 agonist adjuvant PHAD (50 μg). Serum samples were collected pre- and post-IM injection (for up to 10 weeks post 2$^{nd}$ injection) and analyzed by an HAI assay as described in Example 3. HAI assays were carried out for H1N1 and H3N2 and data for H3N2 is presented in FIG. 10 for the three treatment groups. As shown in FIG. 10, the dose-sparing NISV Fluzone® compositions, either adjuvanted with PHAD or unadjuvanted, showed superior immunogenicity compared to the unadjuvanted and unformulated Fluzone® positive control in rhesus macaques up to 10 weeks after the second IM administration.

Example 7

The Role of Lipid:Antigen Ratio, Lipid Concentration and Lipid Content in Thermostability To examine the role that lipids play in thermostability, immunogenic compositions were formulated using the inverted melt method (as described in Example 1) with different lipid:antigen ratios, different lipid content per unit dose and different lipid concentrations during homogenization and reconstitution. The various compositions tested are described in Table 9 below. The aim of this study was to determine the thermostability of the Fluzone® NISV compositions following 3 months storage at 4° C. and 40° C.

TABLE 9

| Group/Test Article | Lipid:Antigen Ratio**** | MPG (mg) | CHO (mg) | DCP (mg) | Concentrated Phosphate Buffer (ml) | Fluzone ® (09/10) (ml) |
|---|---|---|---|---|---|---|
| 1 | 30:1 | 66 | 62.7 | 22 | 0.962 | 50* |
| 2 | 100:1 | 132 | 125.4 | 44 | 0.578 | 30* |
| 3 | 300:1 | 379.48 | 354.04 | 125.08 | 0.578 | 30* |
| 4 | 300:1 | 192.24 | 181.44 | 64.80 | 0.578 | 30** |
| 5 | 300:1 | 756.84 | 708.08 | 250.16 | 0.578 | 30*** |
| 6 | 300:1 | 192.24 | 181.44 | 64.80 | 0.578 | 30** |
| 7 | 300:1 | 756.84 | 708.08 | 250.16 | 0.578 | 30*** |
| 8 | no NISV | N/A | N/A | N/A | N/A | 50* |

*Fluzone ® (2009-2010 season; Sanofi Pasteur) is an inactivated trivalent split influenza vaccine. Each 0.5 ml unit dose of Fluzone ® (2009-2010 season; Sanofi Pasteur) contains 15 μg HA antigen from each of the following influenza virus strains: H1N1, A/Brisbane/59/2007; H3N2, A/Brisbane/10/2007; and B/Brisbane/60/2008 (i.e., 45 μg total HA antigen in 0.5 ml).

**Antigen stock diluted 2 times with 10 mM phosphate buffer, pH 7.2 (i.e., 22.5 μg total HA antigen in 0.5 ml).

***Antigen stock concentrated 2 times with Amicon Ultrafiltration tubes (i.e., 90 μg total HA antigen in 0.5 ml).

****Vesicle forming lipids:HA antigen weight ratio.

The NISVs were composed of the following lipids: 1-monopalmitoyl glycerol (MPG, a non-ionic surfactant), cholesterol (CHO, a steroid) and dicetyl phosphate (DCP, an ionic amphiphile). To maintain a 5:4:1 molar ratio lipid, amounts as given in Table 9 were weighed out and placed in a flat bottom glass beaker and melted in a heated oil bath at 120-125° C. with occasional swirling using a glass rod, as described in Example 1. While the lipids were melting concentrated phosphate buffer in volumes given in Table 9 was added to the appropriate volume of Fluzone® as given in Table 9. The buffered antigen stock solutions were then homogenized at 8,000 rpm at 30-35° C., and quickly (to prevent crystallization) the melted lipids were transferred into the beaker while homogenizing the solution, at which point homogenization at 8,000 rpm continued for 10 minutes at 30-35° C. The resulting NISV-antigen suspensions were shaken for 1-2 hours at 220±10 rpm at 30-35° C. Finally, an equal volume of 400 mM sucrose solution in water was added to the NISV-antigen solutions and shaken for 5 minutes at 220±10 rpm at 30-35° C. Aliquots were taken (1 ml/vial), frozen at −80° C. overnight or longer and subsequently lyophilized according to the target lyophilization parameters in the lyophilization cycle outlined in Table 2 and the primary drying time set points given in Table 3 for different fill volumes.

The compositions (described in Table 10) were stored at 4° C. or 40° C. for up to 3 months, and were then administered IM to mice (as described in Example 2) Immune response in vaccinated mice was determined using the HAI assay described in Example 3. In addition to in vivo potency some additional stability tests as described in Example 4 were conducted on the compositions including visual inspection of the lyophilized cake; measurement of antigen content by sELISA and measurement of moisture content of the lyophilized cake.

TABLE 10

| Group/ Test article (n = 8) | Fluzone ® (09/10)* Content (μg) | Lipid dose (μg) | Lipid:Antigen Ratio**** | Lipid** Concentration Homogenization (mg/ml) | Fill/ Reconstitution volume | Lipid*** Concentration Reconstitution (mg/ml) |
|---|---|---|---|---|---|---|
| 1 | 4.5 | 135 | 30:1 | 2.7 | 1 ml/0.5 ml | 2.7 |
| 2 | 4.5 | 450 | 100:1 | 9 | 1 ml/0.5 ml | 9 |
| 3 | 4.5 | 1350 | 300:1 | 27 | 1 ml/0.5 ml | 27 |
| 4 | 4.5# | 1350 | 300:1 | 13.5 | 1 ml/0.5 ml | 13.5 |
| 5 | 4.5## | 1350 | 300:1 | 54 | 1 ml/0.5 ml | 54 |
| 6 | 4.5# | 1350 | 300:1 | 13.5 | 1 ml/0.25 ml | 27 |
| 7 | 4.5## | 1350 | 300:1 | 54 | 1 ml/1 ml | 27 |
| 8### | 4.5 | N/A | N/A | N/A | N/A | N/A |

*Fluzone ® (2009-2010 season; Sanofi Pasteur) is an inactivated trivalent split influenza vaccine. Each 0.5 ml unit dose of Fluzone ® (2009-2010 season; Sanofi Pasteur) contains 15 μg HA antigen from each of the following influenza virus strains: H1N1, A/Brisbane/59/2007; H3N2, A/Brisbane/10/2007; and B/Brisbane/60/2008 (i.e., 45 μg total HA antigen in 0.5 ml).

**Approximate lipid concentration following homogenization.

***Approximate lipid concentration following reconstitution.

****Vesicle forming lipids:HA antigen weight ratio.

#Diluted antigen stock twice.

Concentrated antigen stock twice.

Commercial Fluzone ® control used without any formulation steps.

The residual moisture in compositions was determined using the Karl Fischer assay and was expressed as percent moisture by weight and is presented in Table 11. There were distinct differences when comparing the residual moisture of the lower lipid:antigen ratio NISV Fluzone® compositions (30:1 and 100:1) versus the higher lipid:antigen ratio NISV Fluzone® compositions (300:1). In general, the low lipid: antigen ratio NISV Fluzone® compositions had higher moisture content (30:1-2.87% and 100:1-1.81%) than the higher lipid:antigen ratio NISV composition (300:1-1.53% or less). We also observed differences in residual moisture in the 300:1 lipid:antigen ratio NISV Fluzone® compositions depending on the lipid concentration during homogenization. Thus, compositions prepared with lower lipid concentrations during homogenization had a residual moisture content in the range of 1.21 to 1.53% (Test articles 3, 4, 6) while compositions prepared with higher lipid concentrations during homogenization had a lower residual moisture content in the range of 0.54 to 0.66% (Test articles 5 and 7). The various lipid:antigen ratios and lipid concentrations can also be expressed as the total lipid content in the lyophilized cake. Using this measurement for lipid content allows for a correlation between lipid content and residual moisture where low lipid content lyophilized cakes have high residual moisture content and high lipid content lyophilized cakes have low residual moisture content. The lipid content in the lyophilized cakes was also compared with the appearance of the cakes after T=0, T=3 months at 4° C. and T=3 months at 40° C. At T=0, all of the NISV Fluzone® composition lyophilized cakes appeared white, well-formed and devoid of micro-collapse, irrespective of lipid content. The same observation was also made for all of the NISV Fluzone® composition lyophilized cakes at T=3 months at 4° C. However, at T=3 months at 40° C., not all of the NISV Fluzone® composition lyophilized cakes appeared intact; the two lowest lipid content lyophilized cakes, i.e., Test article 1 (1.35 mg) and Test article 2 (4.5 mg), appeared to have collapsed and melted back while all of the higher lipid content lyophilized cakes, i.e., Test articles 3-7 (6.75 mg or more) still appeared to be intact, even after storage for three months at this elevated temperature. The same correlations are observed when lipid concentration during homogenization is used instead of lipid content, compare: Test article 1 (2.7 mg/ml) and Test article 2 (9 mg/ml) with Test articles 3-7 (13.5 mg/ml or more).

TABLE 11

| Group/ Test Article | Lipid:Antigen Ratio*** | Lipid** Concentration Homogenization (mg/ml) | Lipid Content (mg)* | Residual Moisture Content (wt %) T = 0 | Visual Inspection T = 0 | Visual Inspection T = 3 months 4° C. | Visual Inspection T = 3 months 40° C. |
|---|---|---|---|---|---|---|---|
| 1 | 30:1 | 2.7 | 1.35 | 2.87 | White well-formed cake | White well-formed cake | Collapsed melted back cake |
| 2 | 100:1 | 9 | 4.5 | 1.81 | White well-formed cake | White well-formed cake | Collapsed melted back cake |
| 3 | 300:1 | 27 | 13.5 | 1.29 | White well-formed cake | White well-formed cake | White well-formed cake |
| 4 | 300:1 | 13.5 | 6.75 | 1.21 | White well-formed cake | White well-formed cake | White well-formed cake |

TABLE 11-continued

| Group/ Test Article | Lipid:Antigen Ratio*** | Lipid** Concentration Homogenization (mg/ml) | Lipid Content (mg)* | Residual Moisture Content (wt %) T = 0 | Visual Inspection T = 0 | T = 3 months 4° C. | T = 3 months 40° C. |
|---|---|---|---|---|---|---|---|
| 5 | 300:1 | 54 | 27 | 0.66 | White well-formed cake | White well-formed cake | White well-formed cake |
| 6 | 300:1 | 13.5 | 6.75 | 1.53 | White well-formed cake | White well-formed cake | White well-formed cake |
| 7 | 300:1 | 54 | 27 | 0.54 | White well-formed cake | White well-formed cake | White well-formed cake |
| 8 | N/A | N/A | N/A | N/A | N/A | N/A | N/A |

*Calculated using lipid concentrations during homogenization and halved due to addition of equal volume of sucrose pre-lyophilization.
**Approximate lipid concentration following homogenization.
***Vesicle forming lipids:HA antigen weight ratio.

FIG. 11 shows in vitro HA antigen content for unformulated commercial Fluzone® (Test article 8) versus a 300:1 lipid:antigen ratio NISV Fluzone® composition (Test article 3), a 100:1 lipid:antigen ratio NISV Fluzone® composition (Test article 2) and a 30:1 lipid:antigen ratio NISV Fluzone® composition (Test article 1). Aliquots of rehydrated compositions were centrifuged in an ultracentrifuge at 24,000 rpm, for 20 minutes at 4° C. and supernatant and pellet fractions were removed, extracted and analyzed by sELISA to determine antigen content (or "in vitro potency") as described in Example 4. Antigen content was determined for the four compositions at T=0 and after three months storage at 40° C. (T=3 months at 40° C.). Significant loss of HA antigen content was detected by sELISA after 3 months storage at 40° C. for both the unformulated Fluzone® control (Test article 8) and the lowest lipid:antigen ratio (30:1) NISV Fluzone® composition (Test article 1). After 3 months storage at 40° C., only 70% of the original HA content remained for commercial Fluzone® while only 40% of the original HA content remained for the lowest lipid:antigen ratio (30:1) NISV Fluzone® composition (Test article 1). In contrast the higher lipid:antigen ratio (100:1 and 300:1) NISV Fluzone® compositions showed very little loss of HA antigen content over time despite being stored at 40° C. for three months.

FIG. 12 shows the in vivo potency in mice (HAI titers assayed as described in Example 3 using sera samples taken 15 days post $2^{nd}$ vaccination) for all of the NISV Fluzone® compositions (Groups 1-7) described in Table 10 versus an unformulated Fluzone® control (Group 8). The results shown are for (A) H1N1 and (B) H3N2 and demonstrate that the NISV Fluzone® compositions and unformulated Fluzone® control were all generally of the same potency at T=0 (average HAI titer for H1N1—189.9; average HAI titer for H3N2—177.5).

FIG. 13 shows the in vivo potency in mice (HAI titers assayed as described in Example 3 using sera samples taken 15 days post $2^{nd}$ vaccination) for the unformulated Fluzone® control (Group 8) versus a 300:1 lipid:antigen ratio NISV Fluzone® composition (Group 3), a 100:1 lipid: antigen ratio NISV Fluzone® composition (Group 2) and a 30:1 lipid:antigen ratio NISV Fluzone® composition (Group 1). All compositions were stored for 3 months at 4° C. or 40° C. prior to IM injection into mice. The results shown are for (A) H1N1 and (B) H3N2 and demonstrate that the 300:1 and 100:1 lipid:antigen ratio NISV Fluzone® compositions (Groups 2 and 3) were equally potent when stored for up to 3 months at 4° C. or 40° C., whereas the unformulated Fluzone® control (Group 8) and the 30:1 lipid:antigen ratio NISV Fluzone® composition (Group 1) lost potency when stored at 40° C. over the same 3 month time period.

FIG. 13 also shows the in vivo potency in mice (HAI titers assayed as described in Example 3 using in sera samples taken 15 days post $2^{nd}$ vaccination) for 300:1 lipid:antigen ratio NISV Fluzone® compositions at three different lipid concentrations during homogenization and reconstitution: low-range lipid concentration (Group 4), mid-range lipid concentration (Group 3) and high-range lipid concentration (Group 5). All compositions were stored for 3 months at 4° C. or 40° C. prior to IM injection into mice. The results shown are for (A) H1N1 and (B) H3N2 and demonstrate that the mid-range and high-range NISV Fluzone® compositions (Groups 3 and 5) were equally potent when stored for up to 3 months at 4° C. or 40° C., whereas the low-range lipid concentration NISV Fluzone® composition (Group 4) showed a minimal loss of potency when stored at 40° C. over the same 3 month time period. The low-range lipid concentration 300:1 lipid:antigen ratio NISV Fluzone® composition (13.5 mg/ml lipid concentration during homogenization) was not as low a lipid concentration as in the 30:1 lipid:antigen ratio NISV Fluzone® composition (2.7 mg/ml lipid concentration during homogenization).

FIG. 13 also shows the in vivo potency in mice (HAI titers assayed, as described in Example 3 using sera samples taken 15 days post $2^{nd}$ vaccination) for 300:1 lipid:antigen ratio NISV Fluzone® compositions at three different lipid concentrations during homogenization and the same lipid concentration at reconstitution: low-range lipid concentration (Group 6), mid-range lipid concentration (Group 3) and high-range lipid concentration (Group 7). All compositions were stored for 3 months at 4° C. or 40° C. prior to IM injection into mice. The results shown are for (A) H1N1 and (B) H3N2 and demonstrate that the mid-range and high-range NISV Fluzone® compositions (Groups 3 and 7) were equally potent when stored for up to 3 months at 4° C. or 40° C., whereas the low-range lipid concentration NISV Fluzone® composition (Group 6) showed a minimal loss of potency when stored at 40° C. over the same 3 month time period. The low-range lipid concentration 300:1 lipid:antigen ratio NISV Fluzone® composition (13.5 mg/ml lipid concentration during homogenization) was not as low a lipid concentration as in the 30:1 lipid:antigen NISV Fluzone® composition (2.7 mg/ml lipid concentration during homogenization).

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. An immunogenic composition comprising an influenza virus hemagglutinin antigen from at least one of influenza A H1N1 and influenza A H3N2 strain and lipid vesicles, wherein the lipid vesicles comprise lipids that are present in the composition in an amount that achieves a lipid:antigen weight ratio within a range of about 50:1 to about 400:1 and the lipids include a non-ionic surfactant comprising 1-monopalmitoyl glycerol, wherein the composition is more stable when stored for 6 months at 40° C. than a reference composition that lacks the lipid vesicles, and (i) wherein the composition comprises one or more inactivated influenza viruses that include the influenza virus hemagglutinin antigen, (ii) wherein the composition comprises one or more attenuated influenza viruses that include the influenza virus hemagglutinin antigen, (iii) wherein the influenza virus hemagglutinin antigen is present in the composition as a split virus antigen, or (iv) wherein the influenza virus hemagglutinin antigen is present in the composition as a purified or recombinant subunit antigen.

2. The composition of claim 1, wherein the composition is a liquid.

3. The composition of claim 1, wherein the composition is dried.

4. The composition of claim 3, wherein the lipid vesicles comprise lipids that are present in the composition in an amount that achieves a lipid: antigen weight ratio of at least about 50:1, and the moisture content of the composition is less than about 2% by weight.

5. The composition of claim 1, wherein the lipid: antigen weight ratio is at least about 100:1.

6. The composition of claim 1, wherein the lipid: antigen weight ratio is at least about 200:1.

7. The composition of claim 1, wherein the lipid: antigen weight ratio is at least about 250:1.

8. The composition of claim 1, wherein the lipid: antigen weight ratio is less than about 350:1.

9. The composition of claim 1, wherein the lipid: antigen weight ratio is within a range of about 250:1 to about 350:1.

10. The composition of claim 1, wherein the lipid: antigen weight ratio is about 300:1.

11. The composition of claim 1, wherein the composition exhibits less than 50% change in immunogenicity as determined by an HAI assay when stored for 6 months at 40° C.

12. The composition of claim 11, wherein the composition exhibits less than 10% change in immunogenicity.

13. The composition of claim 1, wherein the composition exhibits less than 50% loss of antigen content as determined by an ELISA when stored for 6 months at 40° C.

14. The composition of claim 13, wherein the composition exhibits less than 10% loss of antigen content.

15. The composition of claim 1, wherein stability is based on immunogenicity as determined by an HAI assay.

16. The composition of claim 1, wherein stability is based on antigen content as determined by an ELISA.

17. The composition of claim 1, wherein the influenza virus hemagglutinin antigen is from an influenza A H1N1 strain.

18. The composition of claim 1, wherein the influenza virus hemagglutinin antigen is from an influenza A H3N2 strain.

19. The composition of claim 1, wherein the immunogenic composition further comprises an influenza virus hemagglutinin antigen from an influenza B strain.

20. The composition of claim 19, wherein the influenza virus hemagglutinin antigen is from two of an influenza A H1N1 strain, an influenza A H3N2 strain and an influenza B strain.

21. The composition of claim 1, wherein the influenza virus hemagglutinin antigen is from an influenza A H1N1 strain, an influenza A H3N2 strain and combinations of one or both with hemagluttinin antigen from an influenza B strain an influenza B strain.

22. The composition of claim 21, wherein the composition comprises approximately equal amounts of influenza virus hemagglutinin antigen from each strain.

23. The composition of claim 1, wherein the lipids further comprise an ionic amphiphile.

24. The composition of claim 23, wherein the ionic amphiphile is dicetylphosphate.

25. The composition of claim 1, wherein the lipids further comprise a steroid.

26. The composition of claim 25, wherein the steroid is cholesterol.

27. The composition of claim 1, wherein the lipids further comprise an ionic amphiphile and a steroid.

28. The composition of claim 1, wherein the lipids further comprise dicetylphosphate and cholesterol.

29. The composition of claim 1, wherein at least a portion of the influenza virus hemagglutinin antigen present in the composition is associated with the lipid vesicles.

30. The composition of claim 1, wherein at least a portion of the influenza virus hemagglutinin antigen present in the composition is entrapped within the lipid vesicles.

31. The composition of claim 1, wherein the composition further comprises an adjuvant.

32. The composition of claim 31, wherein the adjuvant comprises a TLR-4 agonist.

33. The composition of claim 32, wherein the adjuvant comprises an attenuated lipid A derivative.

34. The composition of claim 32, wherein the adjuvant comprises a monophosphoryl derivative of lipid A.

35. The composition of claim 32, wherein the adjuvant comprises a 3-deacyl monophosphoryl derivative of lipid A.

36. The composition of claim 31, wherein the adjuvant comprises a TLR-7/8 agonist.

37. The composition of claim 31, wherein the adjuvant comprises a TLR-9 agonist.

38. The composition of claim 31, wherein at least a portion of the adjuvant present in the composition is associated with the lipid vesicles.

39. The composition of claim 31, wherein at least a portion of the adjuvant present in the composition is not associated with the lipid vesicles.

40. A method of treating a subject suffering from, or at risk for, an influenza infection, the method comprising:
providing the composition of claim 1 in dried form;
rehydrating the composition; and
administering to the subject a therapeutically effective amount of the rehydrated composition.

41. The method of claim 40, wherein the rehydrated composition is administered by intramuscular injection.

42. A method of preparing an immunogenic composition comprising an influenza virus hemagglutinin antigen from at least one of influenza A H1N1 strain and influenza A H3N2 strain and lipid vesicles, wherein the lipid vesicles comprise lipids that include a non-ionic surfactant comprising 1-monopalmitoyl glycerol, wherein the composition is more stable when stored for 6 months at 40° C. than a reference composition that lacks the lipid vesicles, the method comprising:
melting the lipids to produce molten lipids;
combining the molten lipids with an aqueous solution that includes the influenza virus hemagglutinin antigen; and
homogenizing the resulting product, wherein the molten lipids and aqueous solution are combined in relative amounts that achieve a lipid:antigen weight ratio of at least about 50:1 in the resulting product.

43. The method of claim 42, wherein the molten lipids and aqueous solution are combined in relative amounts that achieve a lipid: antigen weight ratio of at least about 100:1 in the resulting product.

44. The method of claim 42, wherein the molten lipids and aqueous solution are combined in relative amounts that achieve a lipid: antigen weight ratio of at least about 200:1 in the resulting product.

45. The method of claim 42, wherein the molten lipids and aqueous solution are combined in relative amounts that achieve a lipid: antigen weight ratio of at least about 250:1 in the resulting product.

46. The method of claim 42, wherein the molten lipids and aqueous solution are combined in relative amounts that achieve a lipid: antigen weight ratio of less than about 400:1 in the resulting product.

47. The method of claim 42, wherein the molten lipids and aqueous solution are combined in relative amounts that achieve a lipid:antigen weight ratio of less than about 350:1 in the resulting product.

48. The method of claim 42, wherein the molten lipids and aqueous solution are combined in relative amounts that achieve a lipid:antigen weight ratio within a range of about 250:1 to about 350:1 in the resulting product.

49. The method of claim 42, wherein the molten lipids and aqueous solution are combined in relative amounts that achieve a lipid:antigen weight ratio of about 300:1 in the resulting product.

50. The method of claim 42, wherein the molten lipids are added to the aqueous solution that includes the influenza virus hemagglutinin antigen.

51. The method of claim 42, wherein the aqueous solution that includes the influenza virus hemagglutinin antigen is added to the molten lipids.

52. A method of preparing an immunogenic composition comprising an influenza virus hemagglutinin antigen from at least one of influenza A H1N1 strain and influenza A H3N2 strain and lipid vesicles, wherein the lipid vesicles comprise lipids that include a non-ionic surfactant comprising 1-monopalmitoyl glycerol, wherein the composition is more stable when stored for 6 months at 40° C. than a reference composition that lacks the lipid vesicles, the method comprising:
melting the lipids to produce molten lipids;
combining the molten lipids with an aqueous solution that includes the influenza virus hemagglutinin antigen; and
homogenizing the resulting product, wherein the molten lipids and aqueous solution are combined in relative amounts and volumes that achieve a lipid concentration of at least about 10 mg/ml in the resulting product.

53. The method of claim 52, wherein the molten lipids and aqueous solution are combined in relative amounts and volumes that achieve a lipid concentration in a range of about 10 mg/ml to about 100 mg/ml in the resulting product.

54. The method of claim 52, wherein the molten lipids and aqueous solution are combined in relative amounts that achieve a lipid: antigen weight ratio of at least about 50:1 in the resulting product.

55. The method of claim 54, wherein the molten lipids and aqueous solution are combined in relative amounts that achieve a lipid:antigen weight ratio of at least about 100:1 in the resulting product.

56. The method of claim 54, wherein the molten lipids and aqueous solution are combined in relative amounts that achieve a lipid:antigen weight ratio of at least about 200:1 in the resulting product.

57. The method of claim 54, wherein the molten lipids and aqueous solution are combined in relative amounts that achieve a lipid:antigen weight ratio of at least about 250:1 in the resulting product.

58. The method of claim 54, wherein the molten lipids and aqueous solution are combined in relative amounts that achieve a lipid:antigen weight ratio of less than about 400:1 in the resulting product.

59. The method of claim 54, wherein the molten lipids and aqueous solution are combined in relative amounts that achieve a lipid:antigen weight ratio of less than about 350:1 in the resulting product.

60. The method of claim 54, wherein the molten lipids and aqueous solution are combined in relative amounts that achieve a lipid:antigen weight ratio within a range of about 250:1 to about 350:1 in the resulting product.

61. The method of claim 54, wherein the molten lipids and aqueous solution are combined in relative amounts that achieve a lipid:antigen weight ratio of about 300:1 in the resulting product.

62. The method of claim 52, wherein the molten lipids are added to the aqueous solution that includes the influenza virus hemagglutinin antigen.

63. The method of claim 52, wherein the aqueous solution that includes the influenza virus hemagglutinin antigen is added to the molten lipids.

* * * * *

UNITED STATES PATENT AND TRADEMARK OFFICE
CERTIFICATE OF CORRECTION

PATENT NO. : 9,610,248 B2
APPLICATION NO. : 13/808155
DATED : April 4, 2017
INVENTOR(S) : David E. Anderson et al.

It is certified that error appears in the above-identified patent and that said Letters Patent is hereby corrected as shown below:

In the Claims

Column 44, Line 28 (Claim 21, Line 5): delete "an influenza B strain".

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*